United States Patent [19]
Hunter et al.

[11] Patent Number: 5,885,590
[45] Date of Patent: Mar. 23, 1999

[54] ORAL VACCINES COMPRISING MULTIPLE EMULSIONS AND METHODS OF PREPARATION

[76] Inventors: Robert L. Hunter, 3640 Churchwell Ct., Tucker, Ga. 30084; Carol Elizabeth Bennett, 1085-F N. Jamestown Rd., Decatur, Ga. 30033

[21] Appl. No.: 376,088

[22] Filed: Jan. 20, 1995

Related U.S. Application Data

[63] Continuation of Ser. No. 78,551, Jun. 16, 1993, abandoned, which is a continuation of Ser. No. 897,390, Jun. 18, 1992, abandoned, which is a continuation-in-part of Ser. No. 869,822, Apr. 15, 1992, abandoned, which is a continuation of Ser. No. 721,810, Jun. 27, 1991, abandoned.

[51] Int. Cl.⁶ .......................... A61K 45/00; A01N 31/14
[52] U.S. Cl. ................................ 424/280.1; 424/278.1; 424/279.1; 424/283.1; 514/723; 514/772.3
[58] Field of Search ............................ 424/280.1, 278.1, 424/279.1, 283.1; 252/308, 309, 312, 314, 352; 514/723, 772.3

[56] References Cited

U.S. PATENT DOCUMENTS

| | | |
|---|---|---|
| Re. 33,210 | 5/1990 | Stoufer . |
| 3,206,410 | 9/1965 | Möller et al. . |
| 3,234,143 | 2/1966 | Waldmann . |
| 3,255,108 | 6/1966 | Wiese . |
| 3,311,561 | 3/1967 | Anderson et al. . |
| 3,355,394 | 11/1967 | Korbanka et al. . |
| 3,422,842 | 1/1969 | Bonin . |
| 3,489,690 | 1/1970 | Lachampt et al. . |
| 3,565,817 | 2/1971 | Lissant . |
| 3,728,277 | 4/1973 | Foley . |
| 3,776,857 | 12/1973 | Lindner . |
| 3,826,771 | 7/1974 | Anderson et al. . |
| 3,846,546 | 11/1974 | Lachampt et al. . |
| 3,926,840 | 12/1975 | Wendler et al. . |
| 3,957,969 | 5/1976 | Fujiyama et al. . |
| 4,009,117 | 2/1977 | Newingham et al. . |
| 4,026,817 | 5/1977 | Ciuti et al. . |
| 4,035,513 | 7/1977 | Kumano . |
| 4,102,807 | 7/1978 | Iwama et al. . |
| 4,115,548 | 9/1978 | Marsh et al. . |
| 4,122,029 | 10/1978 | Gee et al. . |
| 4,125,603 | 11/1978 | Audibert et al. . |
| 4,184,978 | 1/1980 | France et al. . |
| 4,252,793 | 2/1981 | Altman . |
| 4,350,605 | 9/1982 | Hughett . |
| 4,360,448 | 11/1982 | Li et al. . |
| 4,371,447 | 2/1983 | Webb et al. . |
| 4,384,974 | 5/1983 | Guthauser . |
| 4,385,049 | 5/1983 | Cuca . |
| 4,422,952 | 12/1983 | Koulbanis et al. . |
| 4,446,044 | 5/1984 | Rutkiewic et al. . |
| 4,446,051 | 5/1984 | Berthod et al. . |
| 4,474,912 | 10/1984 | Ozmeral et al. . |
| 4,562,214 | 12/1985 | Barker et al. . |
| 4,584,195 | 4/1986 | Schoolnik et al. . |
| 4,592,859 | 6/1986 | Smith-Johannsen . |
| 4,606,918 | 8/1986 | Allison et al. . |
| 4,690,774 | 9/1987 | Vishnupad et al. . |
| 4,698,178 | 10/1987 | Huttinger et al. . |
| 4,707,470 | 11/1987 | Kirsh et al. . |
| 4,708,753 | 11/1987 | Forsberg . |
| 4,720,353 | 1/1988 | Bell . |
| 4,736,017 | 4/1988 | O'Hanley et al. . |
| 4,737,363 | 4/1988 | Stewart et al. . |
| 4,770,874 | 9/1988 | Allison et al. ............................ 424/88 |
| 4,772,466 | 9/1988 | Allison et al. ............................ 424/88 |
| 4,788,058 | 11/1988 | Parton et al. . |
| 4,793,826 | 12/1988 | Hayes et al. . |
| 4,808,334 | 2/1989 | Ezaki et al. . |
| 4,842,862 | 6/1989 | Jacobs et al. . |
| 4,851,220 | 7/1989 | Yim et al. . |
| 4,880,563 | 11/1989 | Dahms . |
| 4,931,210 | 6/1990 | Takahashi et al. . |
| 4,933,179 | 6/1990 | Allison et al. ............................ 424/89 |
| 4,940,577 | 7/1990 | Greenberg et al. . |
| 4,943,390 | 7/1990 | Hayes et al. . |
| 4,960,814 | 10/1990 | Wu et al. . |
| 4,971,721 | 11/1990 | Takahashi et al. . |
| 4,980,084 | 12/1990 | Vishnupad et al. . |
| 4,985,173 | 1/1991 | Takahashi et al. . |
| 4,985,250 | 1/1991 | Bee et al. . |
| 4,988,456 | 1/1991 | Takahashi et al. . |
| 5,037,653 | 8/1991 | Dawson . |
| 5,061,688 | 10/1991 | Beissinger et al. . |
| 5,114,708 | 5/1992 | Hunter et al. ............................ 514/716 |
| 5,153,312 | 10/1992 | Porro . |

OTHER PUBLICATIONS

Hunter et al., *J. Immunol.*, vol. 133, No. 6, pp. 3167–3175 (1984).
Byars et al., *Vaccine*, vol. 5, pp. 223–227 (1987).
Snippe et al., *Int. Arch. Allergy Appl. Immunol.*, vol. 65, pp. 390–398 (1981).
Hunter et al., *J. Immunol.*, vol. 127, No. 3, pp. 1244–1250 (1981).
Hunter et al., *Immunol. Adjuvants and Vaccines*, G. Gregoriadis et al., eds., Plenum Publ. Corp., pp. 1330140 (1989).
Hunter et al., *Scan. J. Immunol.*, vol. 23, pp. 287–300 (1986).
Becher, Paul, Editor, *Encyclopedia of Emulsion Technology*, vol. 2, pp. 159–238 (1985), Chapter 3 Davis et al "Medical and Pharmaceutical Application of Emulsions".
*Hackh's Chemical Dictionary* (McGraw–Hill, Inc., 1972), p. 431.
Hunter et al (1989) in *Immunological Adjuvants and Vaccines* Gregory Gregoriadis et al eds Plenum Publishing Corp, 1989 pp. 133–144.

*Primary Examiner*—James C. Housel
*Assistant Examiner*—Jennifer Shaver
*Attorney, Agent, or Firm*—Jones & Askew

[57] ABSTRACT

The present invention relates to water-in-oil and water-in-oil-in-water multiple emulsions and methods of preparation which overcome many of the limitations of previous emulsions and are superior preparations for use in numerous applications including, but not limited to, vaccine adjuvants, pharmaceuticals, cosmetics, foods, and various household and industrial uses.

12 Claims, 24 Drawing Sheets

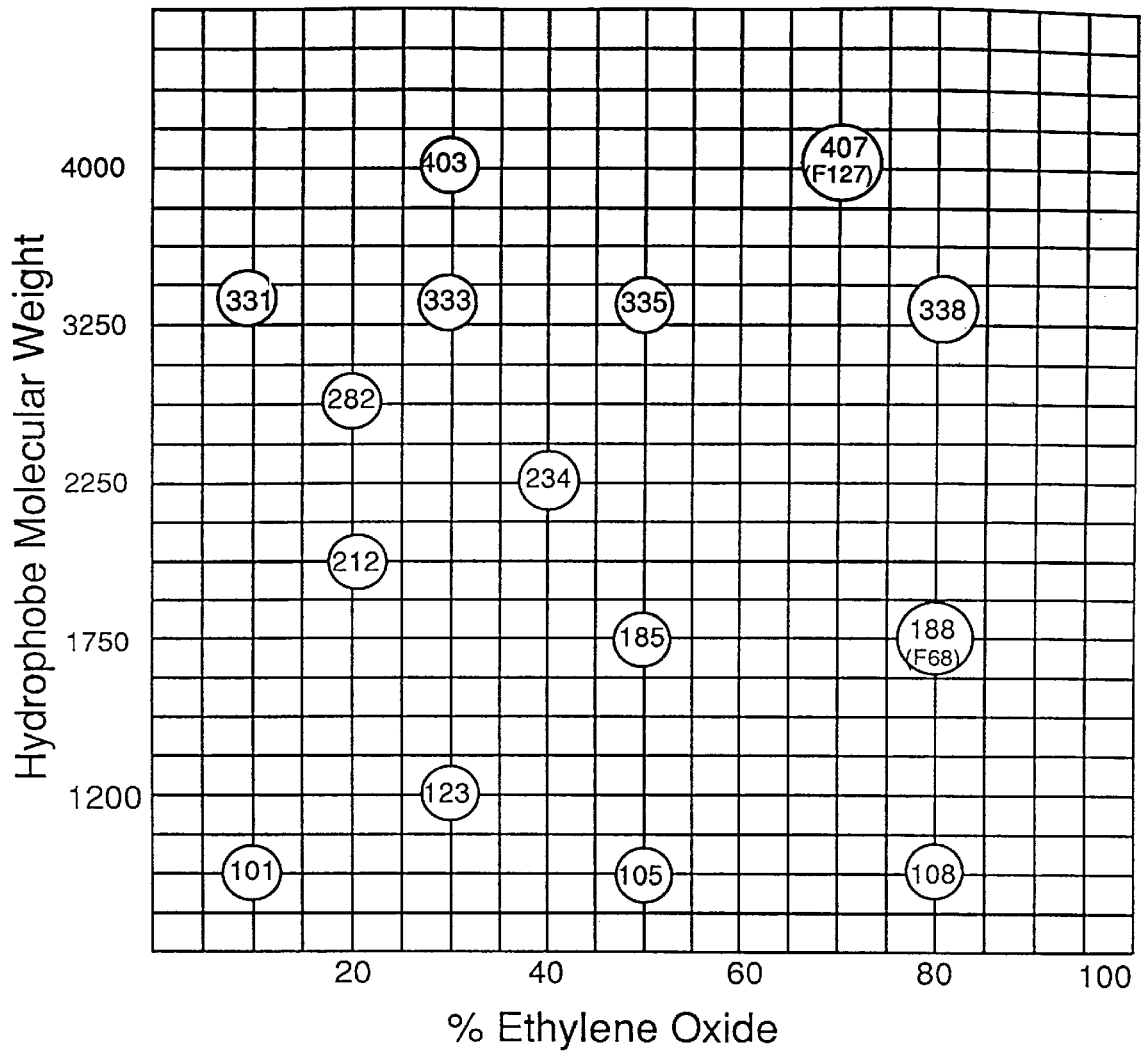
Fig_1

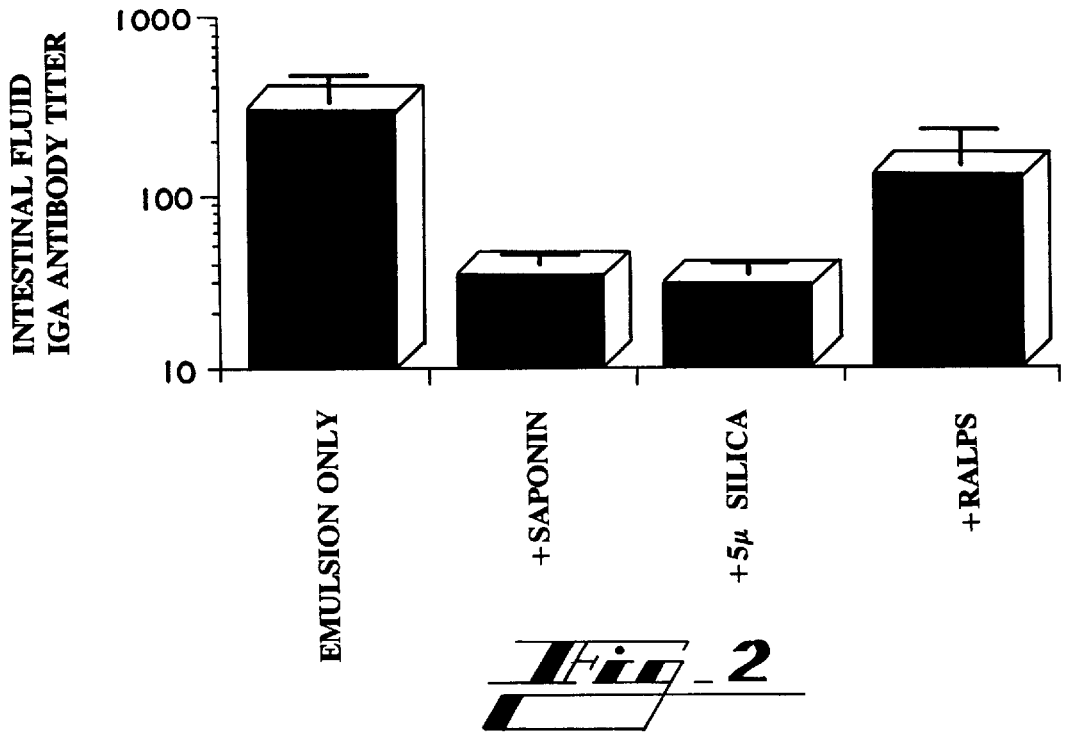
Fig_2
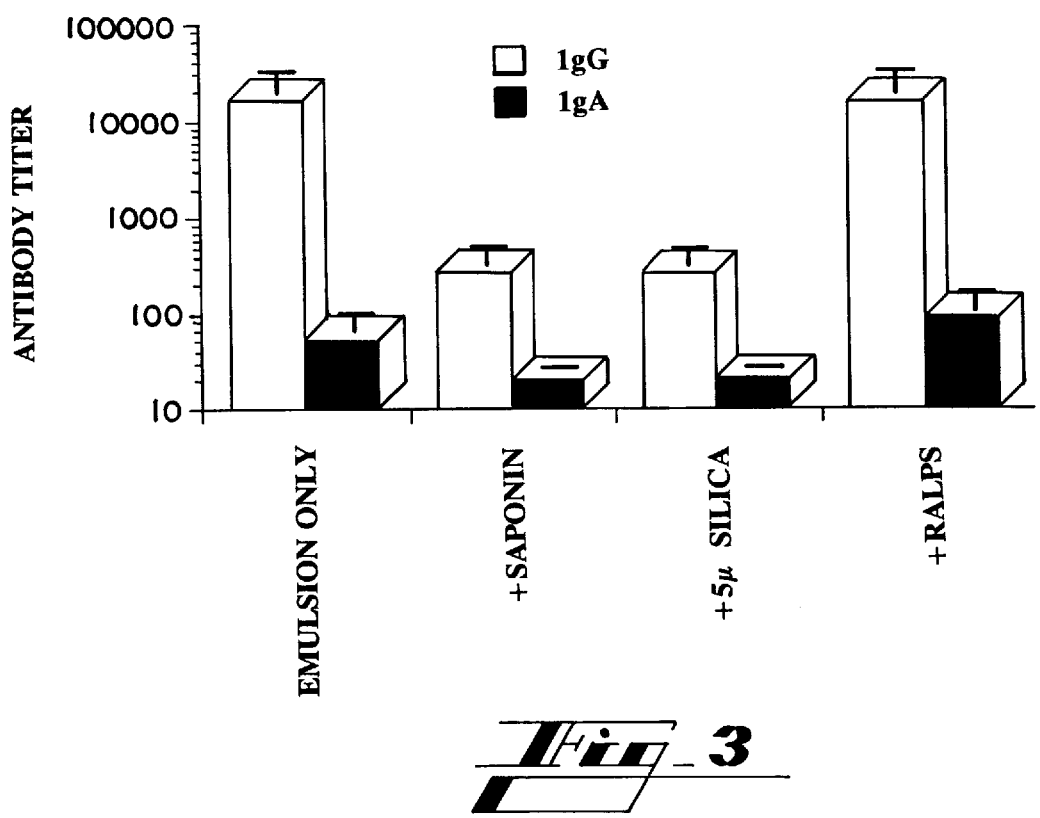
Fig_3

Multiple Emulsions (w-o-w)

| | Water-in-Oil Emulsions | | | | | | | Outer Aqueous Phase | | | | Results | |
|---|---|---|---|---|---|---|---|---|---|---|---|---|---|
| | Inner Aqueous Phase | | | Oil Phase | | | | | | | | | |
| Grp # | Stabi-lizer | Conc | Active | Vol Aq | Type Oil | Vol Oil | Surfactant | % Surf-actant | Stabi-lizer | Surf-actant | %Surf-actant | Vol.Outer Aq | w/o | w/o/w |
| 1 | none | | BSA-3 | 1 | squalene | 1 | L121/S80 | 4/10 | none | nd | nd | nd | 3 | nd |
| 2 | none | | BSA-3 | 1 | squalene | 1 | L121/S80 | 8/10 | none | nd | nd | nd | 0 | nd |
| 3 | none | | BSA-3 | 1 | squalene | 1 | L121/S80 | 12/10 | none | nd | nd | nd | 0 | nd |
| 4 | none | | BSA-3 | 1 | squalene | 1 | L121/S80 | 20/10 | none | nd | nd | nd | 0 | nd |
| 5 | none | | BSA-3 | 1 | squalene | 1 | L141/S80 | 4/10 | none | nd | nd | nd | 3 | nd |
| 6 | none | | BSA-3 | 1 | squalene | 1 | L141/S80 | 8/10 | none | nd | nd | nd | 3 | nd |
| 7 | none | | BSA-3 | 1 | squalene | 1 | L141/S80 | 12/10 | none | nd | nd | nd | 3 | nd |
| 8 | none | | BSA-3 | 1 | squalene | 1 | L141/S80 | 20/10 | none | nd | nd | nd | 0 | nd |
| 9 | none | | BSA-3 | 1 | squalene | 1 | L180.5/S80 | 4/10 | none | nd | nd | nd | 3 | nd |
| 10 | none | | BSA-3 | 1 | squalene | 1 | L180.5/S80 | 8/10 | none | nd | nd | nd | 0 | nd |
| 11 | none | | BSA-3 | 1 | squalene | 1 | L180.5/S80 | 12/10 | none | nd | nd | nd | 0 | nd |
| 12 | none | | BSA-3 | 1 | squalene | 1 | L180.5/S80 | 20/10 | none | nd | nd | nd | 0 | nd |
| 13 | none | | BSA-3 | 9 | squalene | 1 | L121/S80 | 4/10 | none | nd | nd | nd | 0 | nd |
| 14 | none | | BSA-3 | 9 | squalene | 1 | L121/S80 | 8/10 | none | nd | nd | nd | 0 | nd |
| 15 | none | | BSA-3 | 9 | squalene | 1 | L121/S80 | 12/10 | none | nd | nd | nd | 0 | nd |
| 16 | none | | BSA-3 | 9 | squalene | 1 | L121/S80 | 20/10 | none | nd | nd | nd | 0 | nd |

FIGURE 4A

| | Water-in-Oil Emulsions | | | | | | | Multiple Emulsions (w-o-w) | | | | |
|---|---|---|---|---|---|---|---|---|---|---|---|---|
| Inner Aqueous Phase | | | | Oil Phase | | | | Outer Aqueous Phase | | | Results | |
| Grp # | Stabi-lizer | Conc | Active | Vol Aq | Type Oil | Vol Oil | Surfactant | % Surf-actant | Stabi-lizer | Surf-actant | %Surf-actant | Vol. Outer Aq | w/o | w/o/w |
| 17 | none | | BSA-3 | 9 | squalene | 1 | L141/S80 | 8/10 | none | nd | nd | nd | 3 | nd |
| 18 | none | | BSA-3 | 9 | squalene | 1 | L141/S80 | 8/10 | none | nd | nd | nd | 3 | nd |
| 19 | none | | BSA-3 | 9 | squalene | 1 | L141/S80 | 12/10 | none | nd | nd | nd | 3 | nd |
| 20 | none | | BSA-3 | 9 | squalene | 1 | L141/S80 | 20/10 | none | nd | nd | nd | 0 | nd |
| 21 | none | | BSA-3 | 9 | squalene | 1 | L180.5/S80 | 4/10 | none | nd | nd | nd | 3 | nd |
| 22 | none | | BSA-3 | 9 | squalene | 1 | L180.5/S80 | 8/10 | none | nd | nd | nd | 0 | nd |
| 23 | none | | BSA-3 | 9 | squalene | 1 | L180.5/S80 | 12/10 | none | nd | nd | nd | 0 | nd |
| 24 | none | | BSA-3 | 9 | squalene | 1 | L180.5/S80 | 20/10 | none | nd | nd | nd | 0 | nd |
| 25 | none | | BSA-3 | 1 | squalene | 1 | S80 | 10 | none | Tween80/F61 | 0.5/0.5 | 6 | 3 | 0 |
| 26 | none | | BSA-3 | 1 | squalene | 1 | S80 | 20 | none | Tween80/F61 | 0.5/0.5 | 6 | 3 | 0 |
| 27 | none | | BSA-3 | 1 | squalene | 1 | L141/S80 | 20/20 | none | Tween80/F61 | 0.5/0.5 | 6 | 3 | 3 |
| 28 | none | | BSA-3 | 1 | squalene | 1 | L141/S80 | 12/10 | Al St-1 | Tween80/F61 | 0.5/0.5 | 6 | 3 | 3 |
| 29 | none | | BSA-3 | 1 | squalene | 1 | L141/S80 | 20/10 | Al St-4 | Tween80/F61 | 0.5/0.5 | 6 | 3 | 3 |
| 30 | none | | BSA-3 | 1 | squalene | 1 | L141/S80 | 12/10 | Al St-4 | Tween80/F61 | 0.5/0.5 | 6 | 3 | 3 |
| 31 | none | | BSA-3 | 1 | squalene | 1 | L141/S80 | 20/10 | Al St-4 | Tween80/F61 | 0.5/0.5 | 6 | 3 | 3 |
| 32 | L141 | 20% | BSA-3 | 1 | squalene | 1 | S80 | 10 | none | Tween80/F61 | 0.5/0.5 | 6 | 3 | 3 |
| 33 | L180.5 | 20% | BSA-3 | 1 | squalene | 1 | S80 | 10 | none | Tween80/F61 | 0.5/0.5 | 6 | 3 | 3 |
| 34 | L141 | 20% | BSA-3 | 1 | squalene | 1 | S80 | 20 | none | Tween80/F61 | 0.5/0.5 | 6 | 3 | 3 |
| 35 | L180.5 | 20% | BSA-3 | 1 | squalene | 1 | S80 | 20 | none | Tween80/F61 | 0.5/0.5 | 6 | 3 | 3 |

FIGURE 4B

| | Multiple Emulsions (w-o-w) | | | | | | | | | | | |
|---|---|---|---|---|---|---|---|---|---|---|---|---|
| | Water-in-Oil Emulsions | | | | | | | Outer Aqueous Phase | | | | Results |
| | Inner Aqueous Phase | | | Oil Phase | | | | | | | | |
| Grp # | Stabi-lizer | Conc Active | Vol Aq | Type Oil | Vol Oil | Surfactant | % Surf-actant | Stabi-lizer | Surf-actant | %Surf-actant | Vol. Outer Aq | w/o | w/o/w |
| 1 | none | BSA-3 | 1 | squalene | 1 | L141/S80 | 4/10 | sil-10 | Tween 80 | 1 | 2 | 3 | 0 |
| 2 | none | BSA-3 | 1 | squalene | 1 | L141/S80 | 4/10 | sil-10 | Tween 80 | 0.5 | 2 | 3 | 2 |
| 3 | none | BSA-3 | 1 | squalene | 1 | L141/S80 | 4/10 | sil-10 | Tween 80 | 0.25 | 2 | 3 | 3 |
| 4 | none | BSA-3 | 1 | squalene | 1 | L141/S80 | 4/10 | sil-10 | Tween 80 | 0.1 | 2 | 3 | 3 |
| 5 | none | BSA-3 | 1 | squalene | 1 | L141/S80 | 4/10 | sil-10 | F68 | 2 | 2 | 3 | 3 |
| 6 | none | BSA-3 | 1 | squalene | 1 | L141/S80 | 4/10 | sil-10 | F68 | 1 | 2 | 3 | 3 |
| 7 | none | BSA-3 | 1 | squalene | 1 | L141/S80 | 4/10 | sil-10 | F68 | 0.5 | 2 | 3 | 3 |
| 8 | none | BSA-3 | 1 | squalene | 1 | L141/S80 | 4/10 | sil-10 | F68 | 0.25 | 2 | 3 | 3 |
| 9 | none | BSA-3 | 1 | squalene | 1 | L141/S80 | 4/10 | sil-10 | F68 | 0.1 | 2 | 3 | 3 |
| 10 | none | BSA-3 | 1 | squalene | 1 | L141/S80 | 4/10 | sil-10 | Tween 80/F68 | 0.5/0.5 | 2 | 3 | 2 |
| 11 | none | BSA-3 | 1 | squalene | 1 | L141/S80 | 4/10 | sil-10 | Tween 80/F68 | 0.25/0.25 | 2 | 3 | 3 |
| 12 | none | BSA-3 | 1 | squalene | 1 | L141/S80 | 5/10 | | Tween 80/F68 | 0.5/0.5 | 6 | 3 | 2 |
| 13 | none | BSA-3 | 1 | squalene | 1 | L141/S80 | 5/20 | | Tween 80/F68 | 0.5/0.5 | 6 | 3 | 2 |
| 14 | none | BSA-3 | 1 | squalene | 1 | L141/S80 | 5/30 | | Tween 80/F68 | 0.5/0.5 | 6 | 3 | 3 |
| 15 | none | BSA-3 | 1 | squalene | 1 | L141/S80 | 5/40 | | Tween 80/F68 | 0.5/0.5 | 6 | 3 | 2 |

FIGURE 5A

| Multiple Emulsions (w-o-w) ||||||||||||
|---|---|---|---|---|---|---|---|---|---|---|---|
| Water-in-Oil Emulsions |||||||| Outer Aqueous Phase ||| Results ||
| Inner Aqueous Phase |||| Oil Phase |||| | | | | |
| Grp # | Stabi-lizer | Conc | Active | Vol Aq | Type Oil | Vol Oil | Surfactant | % Surf-actant | Stabi-lizer | Surf-actant | %Surf-actant | Vol. Outer Aq | w/o | w/o/w |
| 16 | none | | BSA-3 | 1 | squalene | 1 | L141/S80 | 10/10 | | Tween 80/F68 | 0.5/0.5 | 6 | 3 | 0 |
| 17 | none | | BSA-3 | 1 | squalene | 1 | L141/S80 | 10/20 | | Tween 80/F68 | 0.5/0.5 | 6 | 3 | 0 |
| 18 | none | | BSA-3 | 1 | squalene | 1 | L141/S80 | 10/30 | | Tween 80/F68 | 0.5/0.5 | 6 | 3 | 0 |
| 19 | none | | BSA-3 | 1 | squalene | 1 | L141/S80 | 10/40 | | Tween 80/F68 | 0.5/0.5 | 6 | 3 | 0 |
| 20 | none | | BSA-3 | 1 | squalene | 1 | L180.5/S80 | 5/10 | | Tween 80/F68 | 0.5/0.5 | 6 | 3 | 3 |
| 21 | none | | BSA-3 | 1 | squalene | 1 | L180.5/S80 | 5/20 | | Tween 80/F68 | 0.5/0.5 | 6 | 3 | 3 |
| 22 | none | | BSA-3 | 1 | squalene | 1 | L180.5/S80 | 5/30 | | Tween 80/F68 | 0.5/0.5 | 6 | 3 | 1 |
| 23 | none | | BSA-3 | 1 | squalene | 1 | L180.5/S80 | 5/40 | | Tween 80/F68 | 0.5/0.5 | 6 | 3 | 1 |
| 24 | none | | BSA-3 | 1 | squalene | 1 | L180.5/S80 | 10/10 | | Tween 80/F68 | 0.5/0.5 | 6 | 3 | 3 |
| 25 | none | | BSA-3 | 1 | squalene | 1 | L180.5/S80 | 10/20 | | Tween 80/F68 | 0.5/0.5 | 6 | 3 | 3 |
| 26 | none | | BSA-3 | 1 | squalene | 1 | L180.5/S80 | 10/30 | | Tween 80/F68 | 0.5/0.5 | 6 | 3 | 2 |
| 27 | none | | BSA-3 | 1 | squalene | 1 | L180.5/S80 | 10/40 | | Tween 80/F68 | 0.5/0.5 | 6 | 3 | 0 |

FIGURE 5B

| | Multiple Emulsions (w-o-w) | | | | | | | | | | | | |
|---|---|---|---|---|---|---|---|---|---|---|---|---|---|
| | Water-in-Oil Emulsions | | | | | | | | Outer Aqueous Phase | | | Results | |
| | Inner Aqueous Phase | | | | Oil Phase | | | | | | | | |
| Grp # | Stabi-lizer | Conc | Active | Vol Aq | Type Oil | Vol Oil | Surfactant | % Surf-actant | Stabi-lizer | Surf-actant | %Surf-actant | Vol. Outer Aq | w/o | w/o/w |
| 1 | L180.5 | 10% | BSA-10 | 4 | squalene | 1 | S80 | 10 | none | Tween 80/F68 | 0.5/0.5 | 5 | 3 | 4 |
| 2 | L180.5 | 10% | BSA-10 | 4 | squalene | 1 | S80 | 20 | none | Tween 80/F68 | 0.5/0.5 | 5 | 3 | 4 |
| 3 | L180.5 | 10% | BSA-10 | 4 | squalene | 1 | S80 | 30 | none | Tween 80/F68 | 0.5/0.5 | 5 | 3 | 4 |
| 4 | L141 | 10% | BSA-10 | 4 | squalene | 1 | S80 | 10 | none | Tween 80/F68 | 0.5/0.5 | 5 | 3 | 0 |
| 5 | L141 | 10% | BSA-10 | 4 | squalene | 1 | S80 | 20 | none | Tween 80/F68 | 0.5/0.5 | 5 | 3 | 0 |
| 6 | L141 | 10% | BSA-10 | 4 | squalene | 1 | S80 | 30 | none | Tween 80/F68 | 0.5/0.5 | 5 | 3 | 0 |
| 7 | L180.5 | 10% | BSA-10 | 4 | squalene | 1 | S80 | 10 | none | Tween 80/F68 | 0.25/0.25 | 5 | 3 | 4 |
| 8 | L180.5 | 10% | BSA-10 | 4 | squalene | 1 | S80 | 20 | none | Tween 80/F68 | 0.25/0.25 | 5 | 3 | 4 |
| 9 | L180.5 | 10% | BSA-10 | 4 | squalene | 1 | S80 | 30 | none | Tween 80/F68 | 0.25/0.25 | 5 | 3 | 4 |
| 10 | L141 | 10% | BSA-10 | 4 | squalene | 1 | S80 | 10 | none | Tween 80/F68 | 0.25/0.25 | 5 | 3 | 0 |
| 11 | L141 | 10% | BSA-10 | 4 | squalene | 1 | S80 | 20 | none | Tween 80/F68 | 0.25/0.25 | 5 | 3 | 0 |
| 12 | L141 | 10% | BSA-10 | 4 | squalene | 1 | S80 | 30 | none | Tween 80/F68 | 0.25/0.25 | 5 | 3 | 0 |
| 13 | L180.5 | 10% | BSA-10 | 4 | squalene | 1 | S80 | 10 | none | Tween 80/F68 | 0.5/0.5 | 20 | 3 | 3 |
| 14 | L180.5 | 10% | BSA-10 | 4 | squalene | 1 | S80 | 20 | none | Tween 80/F68 | 0.5/0.5 | 20 | 3 | 3 |
| 15 | L180.5 | 10% | BSA-10 | 4 | squalene | 1 | S80 | 30 | none | Tween 80/F68 | 0.5/0.5 | 20 | 3 | 3 |

FIGURE 6A

| Multiple Emulsions (w-o-w) | | | | | | | | | | | | | | |
|---|---|---|---|---|---|---|---|---|---|---|---|---|---|---|
| Water-in-Oil Emulsions | | | | | | | | | Outer Aqueous Phase | | | Results | | |
| Inner Aqueous Phase | | | | Oil Phase | | | | | | | | | | |
| Grp # | Stabi-lizer | Conc | Active | Vol Aq | Type Oil | Vol Oil | Surfactant | % Surf-actant | Stabi-lizer | Surf-actant | %Surf-actant | Vol. Outer Aq | w/o | w/o/w |
| 16 | L141 | 10% | BSA-10 | 4 | squalene | 1 | S80 | 10 | none | Tween 80/F68 | 0.5/0.5 | 20 | 3 | 0 |
| 17 | L141 | 10% | BSA-10 | 4 | squalene | 1 | S80 | 20 | none | Tween 80/F68 | 0.5/0.5 | 20 | 3 | 0 |
| 18 | L141 | 10% | BSA-10 | 4 | squalene | 1 | S80 | 30 | none | Tween 80/F68 | 0.5/0.5 | 20 | 3 | 0 |
| 19 | L180.5 | 10% | BSA-10 | 4 | squalene | 1 | S80 | 10 | none | Tween 80/F68 | 0.25/0.25 | 20 | 3 | 3 |
| 20 | L180.5 | 10% | BSA-10 | 4 | squalene | 1 | S80 | 20 | none | Tween 80/F68 | 0.25/0.25 | 20 | 3 | 3 |
| 21 | L180.5 | 10% | BSA-10 | 4 | squalene | 1 | S80 | 30 | none | Tween 80/F68 | 0.25/0.25 | 20 | 3 | 3 |
| 22 | L141 | 10% | BSA-10 | 4 | squalene | 1 | S80 | 10 | none | Tween 80/F68 | 0.25/0.25 | 20 | 3 | 0 |
| 23 | L141 | 10% | BSA-10 | 4 | squalene | 1 | S80 | 20 | none | Tween 80/F68 | 0.25/0.25 | 20 | 3 | 0 |
| 24 | L141 | 10% | BSA-10 | 4 | squalene | 1 | S80 | 30 | none | Tween 80/F68 | 0.25/0.25 | 20 | 3 | 3 |

FIGURE 6B

| | | | Multiple Emulsions (w-o-w) | | | | | | | | |
|---|---|---|---|---|---|---|---|---|---|---|---|
| Water-in-Oil Emulsions | | | | | | | | | | | |
| Inner Aqueous Phase | | | Oil Phase | | | | Outer Aqueous Phase | | | Results | |
| Grp # | Stabi-lizer | Conc | Active | Vol Aq | Type Oil | Vol Oil | Surf-actant | % Surf-actant | Stabi-lizer | Surf-actant | %Surf-actant | Vol. Outer Aq | w/o | w/o/w |
| 1 | none | | BSA-3 | 4 | squalene | 1 | none | | none | Tween 80/F68 | 0.25/0.25 | 20 | 0 | nd |
| 2 | none | | BSA-3 | 4 | squalene | 1 | none | | none | Tween 80/F68/P123 | 0.25/0.25/0.5 | 20 | 0 | nd |
| 3 | none | | BSA-3 | 4 | squalene | 1 | none | | none | Tween 80/F68/P123 | 0.25/0.25/0.25 | 20 | 0 | nd |
| 4 | none | | BSA-3 | 4 | squalene | 1 | none | | none | Tween 80/P123 | 0.25/0.25 | 20 | 0 | nd |
| 5 | none | | BSA-3 | 4 | squalene | 1 | none | | none | F68 | 0.25 | 20 | 0 | nd |
| 6 | none | | BSA-3 | 4 | squalene | 1 | none | | none | P123 | 0.25 | 20 | 0 | nd |
| 7 | none | | BSA-3 | 4 | squalene | 1 | S80 | 10 | none | Tween 80/F68 | 0.25/0.25 | 20 | 3 | 3 |
| 8 | none | | BSA-3 | 4 | squalene | 1 | S80 | 10 | none | Tween 80/F68/P123 | 0.25/0.25/0.5 | 20 | 3 | 0 |
| 9 | none | | BSA-3 | 4 | squalene | 1 | S80 | 10 | none | Tween 80/F68/P123 | 0.25/0.25/0.25 | 20 | 3 | 0 |
| 10 | none | | BSA-3 | 4 | squalene | 1 | S80 | 10 | none | Tween 80/P123 | 0.25/0.25 | 20 | 3 | 0 |
| 11 | none | | BSA-3 | 4 | squalene | 1 | S80 | 10 | none | F68 | 0.25 | 20 | 3 | 0 |
| 12 | none | | BSA-3 | 4 | squalene | 1 | S80 | 10 | none | P123 | 0.25 | 20 | 3 | 0 |

FIGURE 7A

| | Water-in-Oil Emulsions | | | | | | | Multiple Emulsions (w-o-w) | | | | | |
|---|---|---|---|---|---|---|---|---|---|---|---|---|---|
| | Inner Aqueous Phase | | | | Oil Phase | | | | Outer Aqueous Phase | | | Results | |
| Grp # | Stabi-lizer | Conc | Active | Vol Aq | Type Oil | Vol Oil | Surf-actant | % Surf-actant | Stabi-lizer | Surf-actant | %Surf-actant | Vol. Outer Aq | w/o | w/o/w |
| 13 | L180.5 | 10% | BSA-3 | 4 | squalene | 1 | none | | none | Tween 80/F68 | 0.25/0.25 | 20 | 0 | nd |
| 14 | L180.5 | 10% | BSA-3 | 4 | squalene | 1 | none | | none | Tween 80/F68/P123 | 0.25/0.25/0.5 | 20 | 0 | nd |
| 15 | L180.5 | 10% | BSA-3 | 4 | squalene | 1 | none | | none | Tween 80/F68/P123 | 0.25/0.25/0.25 | 20 | 0 | nd |
| 16 | L180.5 | 10% | BSA-3 | 4 | squalene | 1 | none | | none | Tween 80/P123 | 0.25/0.25 | 20 | 0 | nd |
| 17 | L180.5 | 10% | BSA-3 | 4 | squalene | 1 | none | | none | F68 | 0.25 | 20 | 0 | nd |
| 18 | L180.5 | 10% | BSA-3 | 4 | squalene | 1 | none | | none | P123 | 0.25 | 20 | 0 | nd |
| 19 | L180.5 | 10% | BSA-3 | 4 | squalene | 1 | S80 | 10 | none | Tween 80/F68 | 0.25/0.25 | 20 | 4 | 3 |
| 20 | L180.5 | 10% | BSA-3 | 4 | squalene | 1 | S80 | 10 | none | Tween 80/F68/P123 | 0.25/0.25/0.5 | 20 | 4 | 3 |
| 21 | L180.5 | 10% | BSA-3 | 4 | squalene | 1 | S80 | 10 | none | Tween 80/F68/P123 | 0.25/0.25/0.25 | 20 | 4 | 3 |
| 22 | L180.5 | 10% | BSA-3 | 4 | squalene | 1 | S80 | 10 | none | Tween 80/P123 | 0.25/0.25 | 20 | 4 | 3 |
| 23 | L180.5 | 10% | BSA-3 | 4 | squalene | 1 | S80 | 10 | none | F68 | 0.25 | 20 | 4 | 2 |
| 24 | L180.5 | 10% | BSA-3 | 4 | squalene | 1 | S80 | 10 | none | P123 | 0.25 | 20 | 4 | 4 |

FIGURE 7B

Multiple Emulsions (w-o-w)

Water-in-Oil Emulsions

| Grp # | Inner Aqueous Phase | | | | Oil Phase | | | | | Outer Aqueous Phase | | | Results | |
|---|---|---|---|---|---|---|---|---|---|---|---|---|---|---|
| | Stabi-lizer | Conc | Active | Vol Aq | Type Oil | Vol Oil | Surf-actant | % Surf-actant | Stabi-lizer | Surf-actant | %Surf-actant | Vol. Outer Aq | w/o | w/o/w |
| 1 | L180.5 | 10% | BSA-3 | 4 | Iso myris | 1 | L101 | 5 | none | P123 | 0.25 | 20 | 0 | 0 |
| 2 | L180.5 | 10% | BSA-3 | 4 | Iso myris | 1 | L101 | 10 | none | P123 | 0.25 | 20 | 0 | 0 |
| 3 | L180.5 | 10% | BSA-3 | 4 | Iso myris | 1 | S80 | 10 | none | P123 | 0.25 | 20 | 0 | 0 |
| 4 | L180.5 | 10% | BSA-3 | 4 | Iso myris | 1 | Arlacel 186 | 10 | none | P123 | 0.25 | 20 | 0 | 0 |
| 5 | L180.5 | 10% | BSA-3 | 4 | Iso myris | 1 | S80 | 10 | AlSt-4 | P123 | 0.25 | 20 | 0 | 0 |
| 6 | | | BSA-3 | 4 | Iso myris | 1 | L101 | 5 | none | P123 | 0.25 | 20 | 0 | 0 |
| 7 | | | BSA-3 | 4 | Iso myris | 1 | L101 | 10 | none | P123 | 0.25 | 20 | 0 | 0 |
| 8 | | | BSA-3 | 4 | Iso myris | 1 | S80 | 10 | none | P123 | 0.25 | 20 | 2 | 0 |
| 9 | | | BSA-3 | 4 | Iso myris | 1 | Arlacel 186 | 10 | none | P123 | 0.25 | 20 | 2 | 0 |
| 10 | | | BSA-3 | 4 | Iso myris | 1 | S80 | 10 | AlSt-4 | P123 | 0.25 | 20 | 2 | 1 |
| 11 | L180.5 | 10% | BSA-3 | 4 | peanut oil | 1 | L101 | 5 | none | P123 | 0.25 | 20 | 0 | 0 |
| 12 | L180.5 | 10% | BSA-3 | 4 | peanut oil | 1 | L101 | 10 | none | P123 | 0.25 | 20 | 0 | 0 |
| 13 | L180.5 | 10% | BSA-3 | 4 | peanut oil | 1 | S80 | 10 | none | P123 | 0.25 | 20 | 3 | 1 |
| 14 | L180.5 | 10% | BSA-3 | 4 | peanut oil | 1 | Arlacel 186 | 10 | none | P123 | 0.25 | 20 | 3 | 1 |
| 15 | L180.5 | 10% | BSA-3 | 4 | peanut oil | 1 | S80 | 10 | AlSt-4 | P123 | 0.25 | 20 | 3 | 1 |

FIGURE 8A

Multiple Emulsions (w-o-w)

Water-in-Oil Emulsions

| | Inner Aqueous Phase | | | | Oil Phase | | | | | Outer Aqueous Phase | | | Results | |
|---|---|---|---|---|---|---|---|---|---|---|---|---|---|---|
| Grp # | Stabi-lizer | Conc | Active | Vol Aq | Type Oil | Vol Oil | Surf-actant | % Surf-actant | Stabi-lizer | Surf-actant | %Surf-actant | Vol. Outer Aq | w/o | w/o/w |
| 16 | | | BSA-3 | 4 | peanut oil | 1 | L101 | 5 | none | P123 | 0.25 | 20 | 0 | 0 |
| 17 | | | BSA-3 | 4 | peanut oil | 1 | L101 | 10 | none | P123 | 0.25 | 20 | 0 | 0 |
| 18 | | | BSA-3 | 4 | peanut oil | 1 | S80 | 10 | none | P123 | 0.25 | 20 | 0 | 0 |
| 19 | | | BSA-3 | 4 | peanut oil | 1 | Arlacel 186 | 10 | none | P123 | 0.25 | 20 | 2 | 0 |
| 20 | | | BSA-3 | 4 | peanut oil | 1 | S80 | 10 | AlSt-4 | P123 | 0.25 | 20 | 2 | 0 |
| 21 | L180.5 | 10% | BSA-3 | 4 | drakeol6VR | 1 | L101 | 5 | none | P123 | 0.25 | 20 | 0 | 0 |
| 22 | L180.5 | 10% | BSA-3 | 4 | drakeol6VR | 1 | L101 | 10 | none | P123 | 0.25 | 20 | 0 | 0 |
| 23 | L180.5 | 10% | BSA-3 | 4 | drakeol6VR | 1 | S80 | 10 | none | P123 | 0.25 | 20 | 2 | 0 |
| 24 | L180.5 | 10% | BSA-3 | 4 | drakeol6VR | 1 | Arlacel 186 | 10 | none | P123 | 0.25 | 20 | 2 | 0 |
| 25 | L180.5 | 10% | BSA-3 | 4 | drakeol6VR | 1 | S80 | 10 | AlSt-4 | P123 | 0.25 | 20 | 2 | 0 |
| 26 | | | BSA-3 | 4 | drakeol6VR | 1 | L101 | 5 | none | P123 | 0.25 | 20 | 0 | 0 |
| 27 | | | BSA-3 | 4 | drakeol6VR | 1 | L101 | 10 | none | P123 | 0.25 | 20 | 0 | 0 |
| 28 | | | BSA-3 | 4 | drakeol6VR | 1 | S80 | 10 | none | P123 | 0.25 | 20 | 0 | 0 |
| 29 | | | BSA-3 | 4 | drakeol6VR | 1 | Arlacel 186 | 10 | none | P123 | 0.25 | 20 | 0 | 0 |
| 30 | | | BSA-3 | 4 | drakeol6VR | 1 | S80 | 10 | AlSt-4 | P123 | 0.25 | 20 | 2 | 1 |

FIGURE 8B

Multiple Emulsions (w-o-w)

| | Inner Aqueous Phase | | | | Water-in-Oil Emulsions | | | | | Outer Aqueous Phase | | | Results | |
|---|---|---|---|---|---|---|---|---|---|---|---|---|---|---|
| | Stabi- | | | Vol | | Vol | Surf- | % Surf- | Stabi- | Surf- | %Surf- | Vol. Outer | | |
| Grp # | lizer | Conc | Active | Aq | Type Oil | Oil | actant | actant | lizer | actant | actant | Aq | w/o | w/o/w |
| 31 | | | BSA-3 | 4 | plurocol2010 | 1 | L101 | 5 | none | P123 | 0.25 | 20 | 0 | 0 |
| 32 | | | BSA-3 | 4 | plurocol2010 | 1 | L101 | 10 | none | P123 | 0.25 | 20 | 0 | 0 |
| 33 | | | BSA-3 | 4 | plurocol2010 | 1 | S80 | 10 | none | P123 | 0.25 | 20 | 0 | 0 |
| 34 | | | BSA-3 | 4 | plurocol2010 | 1 | Arlacel 186 | 10 | none | P123 | 0.25 | 20 | 0 | 0 |
| 35 | | | BSA-3 | 4 | plurocol2010 | 1 | S80 | 10 | AlSt-4 | P123 | 0.25 | 20 | 0 | 0 |
| 36 | | | BSA-3 | 4 | plurocol2010 | 1 | L101 | 5 | none | P123 | 0.25 | 20 | 0 | 0 |
| 37 | | | BSA-3 | 4 | plurocol2010 | 1 | L101 | 10 | none | P123 | 0.25 | 20 | 0 | 0 |
| 38 | | | BSA-3 | 4 | plurocol2010 | 1 | S80 | 10 | none | P123 | 0.25 | 20 | 0 | 0 |
| 39 | | | BSA-3 | 4 | plurocol2010 | 1 | Arlacel 186 | 10 | none | P123 | 0.25 | 20 | 0 | 0 |
| 40 | | | BSA-3 | 4 | plurocol2010 | 1 | S80 | 10 | AlSt-4 | P123 | 0.25 | 20 | 0 | 0 |

FIGURE 8C

Multiple Emulsions (w-o-w)

| | Water-in-Oil Emulsions | | | | | | | | Multiple Emulsions (w-o-w) | | | | Results | | |
|---|---|---|---|---|---|---|---|---|---|---|---|---|---|---|---|
| | Inner Aqueous Phase | | | | Oil Phase | | | | | Outer Aqueous Phase | | | | | |
| Grp # | Stabi-lizer | Conc | Active | Vol Aq | Type Oil | Vol Oil | Surf-actant | % Surf-actant | Stabi-lizer | Surf-actant | %Surf-actant | Vol. Outer Aq | w/o | w/o/w |
| 1 | L141 | 10% | BSA-10 | 1 | peanut oil | 1 | S80 | 10 | Sil-50 | P123 | 0.25 | 2 | 0 | nd |
| 2 | L141 | 10% | BSA-10 | 2.33 | peanut oil | 1 | S80 | 10 | Sil-50 | P123 | 0.25 | 3.33 | o/w | nd |
| 3 | L141 | 10% | BSA-10 | 9 | peanut oil | 1 | S80 | 10 | Sil-50 | P123 | 0.25 | 10 | nd | nd |
| 4 | L180.5 | 10% | BSA-10 | 1 | peanut oil | 1 | S80 | 10 | Sil-50 | P123 | 0.25 | 2 | 2c | 1 |
| 5 | L180.5 | 10% | BSA-10 | 2.33 | peanut oil | 1 | S80 | 10 | Sil-50 | P123 | 0.25 | 3.33 | 2 | 0 |
| 6 | L180.5 | 10% | BSA-10 | 9 | peanut oil | 1 | S80 | 10 | Sil-50 | P123 | 0.25 | 10 | 3 | 2 |
| 7 | L141 | 10% | BSA-10 | 1 | peanut oil | 1 | S80 | 10 | none | P123 | 0.25 | 2 | 0 | nd |
| 8 | L141 | 10% | BSA-10 | 2.33 | peanut oil | 1 | S80 | 10 | none | P123 | 0.25 | 3.33 | o/w | nd |
| 9 | L141 | 10% | BSA-10 | 9 | peanut oil | 1 | S80 | 10 | none | P123 | 0.25 | 10 | nd | nd |
| 10 | L180.5 | 10% | BSA-10 | 1 | peanut oil | 1 | S80 | 10 | none | P123 | 0.25 | 2 | 3c | 3 |
| 11 | L180.5 | 10% | BSA-10 | 2.33 | peanut oil | 1 | S80 | 10 | none | P123 | 0.25 | 3.33 | 3 | 3 |
| 12 | L180.5 | 10% | BSA-10 | 9 | peanut oil | 1 | S80 | 10 | none | P123 | 0.25 | 10 | 3 | 3 |
| 13 | | | BSA-10 | 1 | peanut oil | 1 | S80 | 10 | Sil-50 | P123 | 0.25 | 2 | o/w | nd |
| 14 | | | BSA-10 | 2.33 | peanut oil | 1 | S80 | 10 | Sil-50 | P123 | 0.25 | 3.33 | 0 | nd |
| 15 | | | BSA-10 | 9 | peanut oil | 1 | S80 | 10 | Sil-50 | P123 | 0.25 | 10 | 0 | nd |

FIGURE 9A - 1

Multiple Emulsions (w-o-w)

Water-in-Oil Emulsions

| Grp # | Inner Aqueous Phase | | | | Oil Phase | | | | | | Outer Aqueous Phase | | | Results | | |
|---|---|---|---|---|---|---|---|---|---|---|---|---|---|---|---|---|
| | Stabi-lizer | Conc | Active | Vol Aq | Type Oil | Vol Oil | Surf-actant | % Surf-actant | Stabi-lizer | | Surf-actant | %Surf-actant | Vol. Outer Aq | w/o | w/o | w/o/w |
| 16 | | | BSA-10 | 1 | peanut oil | 1 | S80 | 10 | none | | P123 | 0.25 | 2 | o/w | nd | |
| 17 | | | BSA-10 | 2.33 | peanut oil | 1 | S80 | 10 | none | | P123 | 0.25 | 3.33 | 0 | nd | |
| 18 | | | BSA-10 | 9 | peanut oil | 1 | S80 | 10 | none | | P123 | 0.25 | 10 | 0 | nd | |
| 19 | L141 | 10% | BSA-10 | 1 | peanut oil | 1 | S80 | 10 | Sil-50/AlSt-4 | | P123 | 0.25 | 2 | 2c | 1 | |
| 20 | L141 | 10% | BSA-10 | 2.33 | peanut oil | 1 | S80 | 10 | Sil-50/AlSt-4 | | P123 | 0.25 | 3.33 | o/w | nd | |
| 21 | L141 | 10% | BSA-10 | 9 | peanut oil | 1 | S80 | 10 | Sil-50/AlSt-4 | | P123 | 0.25 | 10 | 0 | nd | |
| 22 | L180.5 | 10% | BSA-10 | 1 | peanut oil | 1 | S80 | 10 | Sil-50/AlSt-4 | | P123 | 0.25 | 2 | 3c | 3 | |
| 23 | L180.5 | 10% | BSA-10 | 2.33 | peanut oil | 1 | S80 | 10 | Sil-50/AlSt-4 | | P123 | 0.25 | 3.33 | 4 | 3 | |
| 24 | L180.5 | 10% | BSA-10 | 9 | peanut oil | 1 | S80 | 10 | Sil-50/AlSt-4 | | P123 | 0.25 | 10 | 4 | 3 | |
| 25 | L141 | 10% | BSA-10 | 1 | peanut oil | 1 | S80 | 10 | AlSt-4 | | P123 | 0.25 | 2 | 0 | nd | |
| 26 | L141 | 10% | BSA-10 | 2.33 | peanut oil | 1 | S80 | 10 | AlSt-4 | | P123 | 0.25 | 3.33 | o/w | nd | |
| 27 | L141 | 10% | BSA-10 | 9 | peanut oil | 1 | S80 | 10 | AlSt-4 | | P123 | 0.25 | 10 | nd | nd | |

FIGURE 9A - 2

| Multiple Emulsions (w-o-w) ||||||||||||
|---|---|---|---|---|---|---|---|---|---|---|---|
| Water-in-Oil Emulsions |||||||||| Outer Aqueous Phase ||| Results ||
| Inner Aqueous Phase |||| Oil Phase ||||| | | Vol. | | |
| Grp # | Stabi-lizer | Conc | Active | Vol Aq | Type Oil | Vol Oil | Surf-actant | % Surf-actant | Stabi-lizer | Surf-actant | %Surf-actant | Outer Aq | w/o | w/o/w |
| 28 | L180.5 | 10% | BSA-10 | 1 | peanut oil | 1 | S80 | 10 | AlSt-4 | P123 | 0.25 | 2 | 3c | 3 |
| 29 | L180.5 | 10% | BSA-10 | 2.33 | peanut oil | 1 | S80 | 10 | AlSt-4 | P123 | 0.25 | 3.33 | 4c | 4 |
| 30 | L180.5 | 10% | BSA-10 | 9 | peanut oil | 1 | S80 | 10 | AlSt-4 | P123 | 0.25 | 10 | 4 | 4 |
| 31 | | | BSA-10 | 1 | peanut oil | 1 | S80 | 10 | Sil-50/AlSt-4 | P123 | 0.25 | 2 | 2 | 1 |
| 32 | | | BSA-10 | 2.33 | peanut oil | 1 | S80 | 10 | Sil-50/AlSt-4 | P123 | 0.25 | 3.33 | 2 | 1 |
| 33 | | | BSA-10 | 9 | peanut oil | 1 | S80 | 10 | Sil-50/AlSt-4 | P123 | 0.25 | 10 | 2 | 0 |
| 34 | | | BSA-10 | 1 | peanut oil | 1 | S80 | 10 | AlSt-4 | P123 | 0.25 | 2 | 2 | 1 |
| 35 | | | BSA-10 | 2.33 | peanut oil | 1 | S80 | 10 | AlSt-4 | P123 | 0.25 | 3.33 | 1 | 1 |
| 36 | | | BSA-10 | 9 | peanut oil | 1 | S80 | 10 | AlSt-4 | P123 | 0.25 | 10 | 2 | 1 |

FIGURE 9A - 3

| | Multiple Emulsions (w-o-w) | | | | | | | | | | | | |
|---|---|---|---|---|---|---|---|---|---|---|---|---|---|
| | Water-in-Oil Emulsions | | | | | | | | | Outer Aqueous Phase | | | Results |
| | Inner Aqueous Phase | | | | Oil Phase | | | | | | | Vol. | |
| Grp # | Stabi-lizer | Conc | Active | Vol Aq | Type Oil | Vol Oil | Surf-actant | % Surf-actant | Stabi-lizer | Surf-actant | %Surf-actant | Outer Aq | w/o | w/o/w |
| 37 | L141 | 10% | CEF | 1 | peanut oil | 1 | S80 | 10 | Sil-50 | P123 | 0.25 | 2 | 0 | nd |
| 38 | L141 | 10% | CEF | 2.33 | peanut oil | 1 | S80 | 10 | Sil-50 | P123 | 0.25 | 3.33 | o/w | nd |
| 39 | L141 | 10% | CEF | 9 | peanut oil | 1 | S80 | 10 | Sil-50 | P123 | 0.25 | 10 | nd | nd |
| 40 | L180.5 | 10% | CEF | 1 | peanut oil | 1 | S80 | 10 | Sil-50 | P123 | 0.25 | 2 | 2 | 2 |
| 41 | L180.5 | 10% | CEF | 2.33 | peanut oil | 1 | S80 | 10 | Sil-50 | P123 | 0.25 | 3.33 | 2 | 2 |
| 42 | L180.5 | 10% | CEF | 9 | peanut oil | 1 | S80 | 10 | Sil-50 | P123 | 0.25 | 10 | 1 | 1 |
| 43 | L141 | 10% | CEF | 1 | peanut oil | 1 | S80 | 10 | none | P123 | 0.25 | 2 | 0 | nd |
| 44 | L141 | 10% | CEF | 2.33 | peanut oil | 1 | S80 | 10 | none | P123 | 0.25 | 3.33 | 0 | nd |
| 45 | L141 | 10% | CEF | 9 | peanut oil | 1 | S80 | 10 | none | P123 | 0.25 | 10 | 0 | nd |
| 46 | L180.5 | 10% | CEF | 1 | peanut oil | 1 | S80 | 10 | none | P123 | 0.25 | 2 | 3c | 3 |
| 47 | L180.5 | 10% | CEF | 2.33 | peanut oil | 1 | S80 | 10 | none | P123 | 0.25 | 3.33 | 3 | 3 |
| 48 | L180.5 | 10% | CEF | 9 | peanut oil | 1 | S80 | 10 | none | P123 | 0.25 | 10 | 3 | 2 |
| 49 | | | CEF | 1 | peanut oil | 1 | S80 | 10 | Sil-50 | P123 | 0.25 | 2 | o/w | nd |
| 50 | | | CEF | 2.33 | peanut oil | 1 | S80 | 10 | Sil-50 | P123 | 0.25 | 3.33 | nd | nd |
| 51 | | | CEF | 9 | peanut oil | 1 | S80 | 10 | Sil-50 | P123 | 0.25 | 10 | nd | nd |

FIGURE 9B - 1

| | Multiple Emulsions (w-o-w) | | | | | | | | | | | | |
|---|---|---|---|---|---|---|---|---|---|---|---|---|---|
| | Water-in-Oil Emulsions | | | | | | | | | Outer Aqueous Phase | | | Results |
| | Inner Aqueous Phase | | | | Oil Phase | | | | | | | | |
| Grp # | Stabi-lizer | Conc | Active | Vol Aq | Type Oil | Vol Oil | Surf-actant | % Surf-actant | Stabi-lizer | Surf-actant | %Surf-actant | Vol. Outer Aq | w/o | w/o/w |
| 52 | | | CEF | 1 | peanut oil | 1 | S80 | 10 | none | P123 | 0.25 | 2 | o/w | nd |
| 53 | | | CEF | 2.33 | peanut oil | 1 | S80 | 10 | none | P123 | 0.25 | 3.33 | nd | nd |
| 54 | | | CEF | 9 | peanut oil | 1 | S80 | 10 | none | P123 | 0.25 | 10 | nd | nd |
| 55 | L141 | 10% | CEF | 1 | peanut oil | 1 | S80 | 10 | Sil-50/AlSt-4 | P123 | 0.25 | 2 | 1 | 0 |
| 56 | L141 | 10% | CEF | 2.33 | peanut oil | 1 | S80 | 10 | Sil-50/AlSt-4 | P123 | 0.25 | 3.33 | o/w | nd |
| 57 | L141 | 10% | CEF | 9 | peanut oil | 1 | S80 | 10 | Sil-50/AlSt-4 | P123 | 0.25 | 10 | nd | nd |
| 58 | L180.5 | 10% | CEF | 1 | peanut oil | 1 | S80 | 10 | Sil-50/AlSt-4 | P123 | 0.25 | 2 | 3c | 3 |
| 59 | L180.5 | 10% | CEF | 2.33 | peanut oil | 1 | S80 | 10 | Sil-50/AlSt-4 | P123 | 0.25 | 3.33 | 3 | 3 |
| 60 | L180.5 | 10% | CEF | 9 | peanut oil | 1 | S80 | 10 | Sil-50/AlSt-4 | P123 | 0.25 | 10 | 4 | 3 |
| 61 | L141 | 10% | CEF | 1 | peanut oil | 1 | S80 | 10 | AlSt-4 | P123 | 0.25 | 2 | 2 | 1 |
| 62 | L141 | 10% | CEF | 2.33 | peanut oil | 1 | S80 | 10 | AlSt-4 | P123 | 0.25 | 3.33 | o/w | nd |
| 63 | L141 | 10% | CEF | 9 | peanut oil | 1 | S80 | 10 | AlSt-4 | P123 | 0.25 | 10 | nd | nd |

FIGURE 9B - 2

| | Multiple Emulsions (w-o-w) | | | | | | | | | | | |
|---|---|---|---|---|---|---|---|---|---|---|---|---|
| | Water-in-Oil Emulsions | | | | | | | Outer Aqueous Phase | | | Results | |
| | Inner Aqueous Phase | | | | Oil Phase | | | | | | | |
| | | | | | | | % | | | Vol. | | |
| Grp # | Stabi- lizer | Conc | Active | Vol Aq | Type Oil | Vol Oil | Surf- actant | Surf- actant | Stabi- lizer | Surf- actant | %Surf- actant | Outer Aq | w/o | w/o/w |
| 64 | L180.5 | 10% | CEF | 1 | peanut oil | 1 | S80 | 10 | AlSt-4 | P123 | 0.25 | 2 | 3c | 3 |
| 65 | L180.5 | 10% | CEF | 2.33 | peanut oil | 1 | S80 | 10 | AlSt-4 | P123 | 0.25 | 3.33 | 4c | 3 |
| 66 | L180.5 | 10% | CEF | 9 | peanut oil | 1 | S80 | 10 | AlSt-4 | P123 | 0.25 | 10 | 4 | 4 |
| 67 | | | CEF | 1 | peanut oil | 1 | S80 | 10 | Sil-50/AlSt-4 | P123 | 0.25 | 2 | o/w | nd |
| 68 | | | CEF | 2.33 | peanut oil | 1 | S80 | 10 | Sil-50/AlSt-4 | P123 | 0.25 | 3.33 | nd | nd |
| 69 | | | CEF | 9 | peanut oil | 1 | S80 | 10 | Sil-50/AlSt-4 | P123 | 0.25 | 10 | nd | nd |
| 70 | | | CEF | 1 | peanut oil | 1 | S80 | 10 | AlSt-4 | P123 | 0.25 | 2 | o/w | nd |
| 71 | | | CEF | 2.33 | peanut oil | 1 | S80 | 10 | AlSt-4 | P123 | 0.25 | 3.33 | nd | nd |
| 72 | | | CEF | 9 | peanut oil | 1 | S80 | 10 | AlSt-4 | P123 | 0.25 | 10 | nd | nd |

FIGURE 9B - 3

Multiple Emulsions (w-o-w)

Water-in-Oil Emulsions

| | Inner Aqueous Phase | | | | Oil Phase | | | | | Outer Aqueous Phase | | | Results | |
|---|---|---|---|---|---|---|---|---|---|---|---|---|---|---|
| Grp # | Stabi- lizer | Conc | Active | Vol Aq | Type Oil | Vol Oil | Surf- actant | % Surf- actant | Stabi- lizer | Surf- actant | %Surf- actant | Vol. Outer Aq | w/o | w/o/w |
| 1 | none | | BSA-10 | 2.33 | squalene | 1 | S80 | 10 | none | P123 | 0.25 | 3.33 | 3 | 0 |
| 2 | L180.5 | 10% | BSA-10 | 2.33 | squalene | 1 | S80 | 10 | none | P123 | 0.25 | 3.33 | 3c | 3 |
| 3 | 31R1 | 10% | BSA-10 | 2.33 | squalene | 1 | S80 | 10 | none | P123 | 0.25 | 3.33 | 0 | nd |
| 4 | T1501 | 10% | BSA-10 | 2.33 | squalene | 1 | S80 | 10 | none | P123 | 0.25 | 3.33 | 3 | 2 |
| 5 | T150R1 | 10% | BSA-10 | 2.33 | squalene | 1 | S80 | 10 | none | P123 | 0.25 | 3.33 | 0 | nd |
| 6 | Span 65 | 10% | BSA-10 | 2.33 | squalene | 1 | S80 | 10 | none | P123 | 0.25 | 3.33 | 4 | 0 |
| 7 | egg lec | 10% | BSA-10 | 2.33 | squalene | 1 | S80 | 10 | none | P123 | 0.25 | 3.33 | 0 | nd |
| 8 | soy lec | 10% | BSA-10 | 2.33 | squalene | 1 | S80 | 10 | none | P123 | 0.25 | 3.33 | 3 | 0 |
| 9 | DDA | 10% | BSA-10 | 2.33 | squalene | 1 | S80 | 10 | none | P123 | 0.25 | 3.33 | 4 | w/o |
| 10 | AlSt | 10% | BSA-10 | 2.33 | squalene | 1 | S80 | 10 | none | P123 | 0.25 | 3.33 | 4 | 0 |
| 11 | Octadecyl | 10% | BSA-10 | 2.33 | squalene | 1 | S80 | 10 | none | P123 | 0.25 | 3.33 | 4 | 0 |
| 12 | Palmi Acid | 10% | BSA-10 | 2.33 | squalene | 1 | S80 | 10 | none | P123 | 0.25 | 3.33 | nd | nd |

FIGURE 10A

Multiple Emulsions (w-o-w)

Water-in-Oil Emulsions

| Grp # | Inner Aqueous Phase | | | | Oil Phase | | | | | Outer Aqueous Phase | | | Results | |
|---|---|---|---|---|---|---|---|---|---|---|---|---|---|---|
| | Stabi-lizer | Conc | Active | Vol Aq | Type Oil | Vol Oil | Surf-actant | % Surf-actant | Stabi-lizer | Surf-actant | %Surf-actant | Vol. Outer Aq | w/o | w/o/w |
| 13 | none | | BSA-10 | 2.33 | peanut oil | 1 | S80 | 10 | none | P123 | 0.25 | 3.33 | 0 | 0 |
| 14 | L180.5 | 10% | BSA-10 | 2.33 | peanut oil | 1 | S80 | 10 | none | P123 | 0.25 | 3.33 | 3 | 3 |
| 15 | 31R1 | 10% | BSA-10 | 2.33 | peanut oil | 1 | S80 | 10 | none | P123 | 0.25 | 3.33 | 0 | nd |
| 16 | T1501 | 10% | BSA-10 | 2.33 | peanut oil | 1 | S80 | 10 | none | P123 | 0.25 | 3.33 | 3 | 0 |
| 17 | T150R1 | 10% | BSA-10 | 2.33 | peanut oil | 1 | S80 | 10 | none | P123 | 0.25 | 3.33 | nd | nd |
| 18 | Span 65 | 10% | BSA-10 | 2.33 | peanut oil | 1 | S80 | 10 | none | P123 | 0.25 | 3.33 | 0 | nd |
| 19 | egg lec | 10% | BSA-10 | 2.33 | peanut oil | 1 | S80 | 10 | none | P123 | 0.25 | 3.33 | 3 | 0 |
| 20 | soy lec | 10% | BSA-10 | 2.33 | peanut oil | 1 | S80 | 10 | none | P123 | 0.25 | 3.33 | 3 | 0 |
| 21 | DDA | 10% | BSA-10 | 2.33 | peanut oil | 1 | S80 | 10 | none | P123 | 0.25 | 3.33 | 4 | w/o |
| 22 | Al St | 10% | BSA-10 | 2.33 | peanut oil | 1 | S80 | 10 | none | P123 | 0.25 | 3.33 | 0 | nd |
| 23 | Octadecyl | 10% | BSA-10 | 2.33 | peanut oil | 1 | S80 | 10 | none | P123 | 0.25 | 3.33 | o/w | nd |
| 24 | Palmi Acid | 10% | BSA-10 | 2.33 | peanut oil | 1 | S80 | 10 | none | P123 | 0.25 | 3.33 | nd | nd |

FIGURE 10B

Multiple Emulsions (w-o-w)

Water-in-Oil Emulsions

| | Inner Aqueous Phase | | | | Oil Phase | | | | | Outer Aqueous Phase | | | Results | |
|---|---|---|---|---|---|---|---|---|---|---|---|---|---|---|
| Grp # | Stabi-lizer | Conc | Active | Vol Aq | Type Oil | Vol Oil | Surf-actant | % Surf-actant | Stabi-lizer | Surf-actant | %Surf-actant | Vol. Outer Aq | w/o | w/o/w |
| 25 | none | | BSA-10 | 2.33 | drakeol6VR | 1 | S80 | 10 | none | P123 | 0.25 | 3.33 | 0 | 0 |
| 26 | L180.5 | 10% | BSA-10 | 2.33 | drakeol6VR | 1 | S80 | 10 | none | P123 | 0.25 | 3.33 | 3 | 3 |
| 27 | 31R1 | 10% | BSA-10 | 2.33 | drakeol6VR | 1 | S80 | 10 | none | P123 | 0.25 | 3.33 | 0 | nd |
| 28 | T1501 | 10% | BSA-10 | 2.33 | drakeol6VR | 1 | S80 | 10 | none | P123 | 0.25 | 3.33 | 3 | 1 |
| 29 | T150R1 | 10% | BSA-10 | 2.33 | drakeol6VR | 1 | S80 | 10 | none | P123 | 0.25 | 3.33 | 0 | nd |
| 30 | Span 65 | 10% | BSA-10 | 2.33 | drakeol6VR | 1 | S80 | 10 | none | P123 | 0.25 | 3.33 | 0 | nd |
| 31 | egg lec | 10% | BSA-10 | 2.33 | drakeol6VR | 1 | S80 | 10 | none | P123 | 0.25 | 3.33 | 0 | nd |
| 32 | soy lec | 10% | BSA-10 | 2.33 | drakeol6VR | 1 | S80 | 10 | none | P123 | 0.25 | 3.33 | 2 | 0 |
| 33 | DDA | 10% | BSA-10 | 2.33 | drakeol6VR | 1 | S80 | 10 | none | P123 | 0.25 | 3.33 | 4 | w/o |
| 34 | Al St | 10% | BSA-10 | 2.33 | drakeol6VR | 1 | S80 | 10 | none | P123 | 0.25 | 3.33 | 0 | nd |
| 35 | Octadecyl | 10% | BSA-10 | 2.33 | drakeol6VR | 1 | S80 | 10 | none | P123 | 0.25 | 3.33 | 1 | 0 |
| 36 | Palmi Acid | 10% | BSA-10 | 2.33 | drakeol6VR | 1 | S80 | 10 | none | P123 | 0.25 | 3.33 | nd | nd |

FIGURE 10C

| | | | | Multiple Emulsions (w-o-w) | | | | | | | | | |
|---|---|---|---|---|---|---|---|---|---|---|---|---|---|
| | | | | Water-in-Oil Emulsions | | | | | | Outer Aqueous Phase | | | Results |
| | Inner Aqueous Phase | | | | Oil Phase | | | | | | | Vol. | |
| Grp # | Stabi-lizer | Conc | Active | Vol Aq | Type Oil | Vol Oil | Surf-actant | % Surf-actant | Stabi-lizer | Surf-actant | %Surf-actant | Outer Aq | w/o | w/o/w |
| 37 | none | | BSA-10 | 2.33 | iso myris | 1 | S80 | 10 | none | P123 | 0.25 | 3.33 | 2 | 0 |
| 38 | L180.5 | 10% | BSA-10 | 2.33 | iso myris | 1 | S80 | 10 | none | P123 | 0.25 | 3.33 | 3 | 3 |
| 39 | 31R1 | 10% | BSA-10 | 2.33 | iso myris | 1 | S80 | 10 | none | P123 | 0.25 | 3.33 | 0 | nd |
| 40 | T1501 | 10% | BSA-10 | 2.33 | iso myris | 1 | S80 | 10 | none | P123 | 0.25 | 3.33 | 2 | 1 |
| 41 | T150R1 | 10% | BSA-10 | 2.33 | iso myris | 1 | S80 | 10 | none | P123 | 0.25 | 3.33 | 0 | nd |
| 42 | Span 65 | 10% | BSA-10 | 2.33 | iso myris | 1 | S80 | 10 | none | P123 | 0.25 | 3.33 | 0 | nd |
| 43 | egg lec | 10% | BSA-10 | 2.33 | iso myris | 1 | S80 | 10 | none | P123 | 0.25 | 3.33 | 0 | nd |
| 44 | soy lec | 10% | BSA-10 | 2.33 | iso myris | 1 | S80 | 10 | none | P123 | 0.25 | 3.33 | 2 | 0 |
| 45 | DDA | 10% | BSA-10 | 2.33 | iso myris | 1 | S80 | 10 | none | P123 | 0.25 | 3.33 | 3 | w/o |
| 46 | Al St | 10% | BSA-10 | 2.33 | iso myris | 1 | S80 | 10 | none | P123 | 0.25 | 3.33 | 0 | nd |
| 47 | Octadecyl | 10% | BSA-10 | 2.33 | iso myris | 1 | S80 | 10 | none | P123 | 0.25 | 3.33 | 1 | 0 |
| 48 | Palmi Acid | 10% | BSA-10 | 2.33 | iso myris | 1 | S80 | 10 | none | P123 | 0.25 | 3.33 | nd | nd |

FIGURE 10D

Multiple Emulsions (w-o-w)

Water-in-Oil Emulsions

| Grp | Inner Aqueous Phase | | | | Oil Phase | | | | | Outer Aqueous Phase | | | Results | |
|---|---|---|---|---|---|---|---|---|---|---|---|---|---|---|
| # | Stabi-lizer | Conc | Active | Vol Aq | Type Oil | Vol Oil | Surf-actant | % Surf-actant | Stabi-lizer | Surf-actant | %Surf-actant | Vol. Outer Aq | w/o | w/o/w |
| 1  | L180.5 | 10.00% | BSA-3  | 4 | squalene | 1 | S80 | 10 | none | P123 | 0.25 | 20 | 4 | 4 |
| 2  | L180.5 | 5.00%  | BSA-3  | 4 | squalene | 1 | S80 | 10 | none | P123 | 0.25 | 20 | 4 | 4 |
| 3  | L180.5 | 2.50%  | BSA-3  | 4 | squalene | 1 | S80 | 10 | none | P123 | 0.25 | 20 | 4 | 3 |
| 4  | L180.5 | 1.25%  | BSA-3  | 4 | squalene | 1 | S80 | 10 | none | P123 | 0.25 | 20 | 4 | 2 |
| 5  | L180.5 | 0.50%  | BSA-3  | 4 | squalene | 1 | S80 | 10 | none | P123 | 0.25 | 20 | 4 | 2 |
| 6  | L180.5 | 0.25%  | BSA-3  | 4 | squalene | 1 | S80 | 10 | none | P123 | 0.25 | 20 | 4 | 1 |
| 7  | L180.5 | 0.10%  | BSA-3  | 4 | squalene | 1 | S80 | 10 | none | P123 | 0.25 | 20 | 4 | 1 |
| 8  | L180.5 | 0.05%  | BSA-3  | 4 | squalene | 1 | S80 | 10 | none | P123 | 0.25 | 20 | 4 | 1 |
| 9  | L180.5 | 0.01%  | BSA-3  | 4 | squalene | 1 | S80 | 10 | none | P123 | 0.25 | 20 | 4 | 0.5 |
| 10 | L180.5 | 0.00%  | BSA-3  | 4 | squalene | 1 | S80 | 10 | none | P123 | 0.25 | 20 | 4 | 0 |
| 11 | L180.5 | 10.00% | saline | 4 | squalene | 1 | S80 | 10 | none | P123 | 0.25 | 20 | 4 | 4 |
| 12 | L180.5 | 5.00%  | saline | 4 | squalene | 1 | S80 | 10 | none | P123 | 0.25 | 20 | 4 | 4 |
| 13 | L180.5 | 2.50%  | saline | 4 | squalene | 1 | S80 | 10 | none | P123 | 0.25 | 20 | 4 | 3 |
| 14 | L180.5 | 1.25%  | saline | 4 | squalene | 1 | S80 | 10 | none | P123 | 0.25 | 20 | 4 | 2 |
| 15 | L180.5 | 0.50%  | saline | 4 | squalene | 1 | S80 | 10 | none | P123 | 0.25 | 20 | 4 | 2 |
| 16 | L180.5 | 0.25%  | saline | 4 | squalene | 1 | S80 | 10 | none | P123 | 0.25 | 20 | 4 | 1 |
| 17 | L180.5 | 0.10%  | saline | 4 | squalene | 1 | S80 | 10 | none | P123 | 0.25 | 20 | 4 | 1 |
| 18 | L180.5 | 0.05%  | saline | 4 | squalene | 1 | S80 | 10 | none | P123 | 0.25 | 20 | 4 | 1 |
| 19 | L180.5 | 0.01%  | saline | 4 | squalene | 1 | S80 | 10 | none | P123 | 0.25 | 20 | 4 | 0.5 |
| 20 | L180.5 | 0.00%  | saline | 4 | squalene | 1 | S80 | 10 | none | P123 | 0.25 | 20 | 4 | 0 |

FIGURE 11

ORAL VACCINES COMPRISING MULTIPLE EMULSIONS AND METHODS OF PREPARATION

CROSS-REFERENCE TO RELATED APPLICATIONS

This is a continuation of U.S. patent application Ser. No. 08/078,551, filed Jun. 16, 1993, now abandoned, which is a continuation of U.S. patent application Ser. No. 07/897,390, filed Jun. 18, 1992, now abandoned, which is a continuation-in-part of application Ser. No. 07/869,822, filed Apr. 15, 1992, now abandoned, which is a continuation of application Ser. No. 07/721,810, filed Jun. 27, 1991, now abandoned.

TECHNICAL FIELD

The present invention relates to compositions and methods for preparing water-in-oil and water-in-oil-in-water multiple emulsions. More particularly, the present invention relates to compositions and methods for preparing stable water-in-oil multiple emulsions which are useful for many different applications, including, but not limited to, adjuvants; vaccines, including oral and perental immunization; oral, topical and parenteral drug delivery; and cosmetics.

BACKGROUND OF THE INVENTION

An emulsion is a heterogeneous system consisting of at least two immiscible liquids, one of which is dispersed in the other in the form of droplets. Such systems possess minimal stability.[1] The problem of stability of the emulsion has conventionally been addressed by the addition of additives such as emulsifiers and finely divided solids. Emulsions consist of continuous and discontinuous phases. The discontinuous phase is referred to variously as the dispersed or internal phase, whereas the phase in which the dispersion occurs is referred to as the continuous or external phase. The standard components of emulsions are an oily and an aqueous phase. When water is the continuous phase, the emulsion is referred to as oil-in-water (o/w), and when oil is the continuous phase, the emulsion is referred to as water-in-oil (w/o). Multi-phase emulsions of water-in-oil-in-water (w/o/w) have gained an importance recently.

Oil-in-water emulsions are the most frequently used emulsions. However, water-in-oil and multiple emulsions are desirable for many applications and would be more extensively used if the problems with instability could be overcome. The Encyclopedia of Emulsion Technology states "Multiple (or double) emulsions are used as depot systems and can be considered as a variation of W/O type. Their potential advantages in drug delivery can be counterbalanced by an increased complexity of the dosage form and the attendant problems of optimal formulation and acceptable stability."[2] W/O is an abbreviation for water-in-oil. "Despite their early promise, the multiple-emulsion system has not been widely utilized. . . . Multiple emulsions produced from vegetable oils are particularly difficult to make if a high yield of multiple droplets and good stability are required."

Emulsions generally consist of three components. The oil phase, the aqueous phase, and an emulsifier. Each of these components and the method in which they are prepared and combined contributes to the type and stability of emulsion. Many attempts have been made to define rules which determine the type of emulsion produced.[3] In general, the liquid (oil or water) in which the surfactant is most soluble will be the continuous phase in the final emulsion. However, correlations between the properties of surfactant, oil and other materials, and emulsification are very empirical. That is, the rules apply to a limited spectrum of materials and there are frequent exceptions.[4]

The mode of mixing the components is important in determining the properties of emulsions. There are three general means of emulsification: 1) Mechanical, 2) Phase inversion, and 3) Spontaneous emulsification.[5]

Mechanical emulsification which uses shear force to break the emulsion components into small particles is the most commonly used. Phase inversion refers to the process of producing an emulsion of one type, water-in-oil, with components which are most stable with the opposite type, oil-in-water. The emulsion then spontaneously changes type. These emulsions can be critically dependent upon concentration of materials, salts, temperature and other factors. Spontaneous emulsification refers to the situation where an emulsion is formed with minimal agitation.[6] This implies a level of thermodynamic stability which is highly desirable, but seldom achieved.

Surface active agents are compounds which contain a hydrophilic and hydrophobic moiety in the same molecule. They preferentially localize at interfaces between oil and water where they reduce the surface-free energy. Within the spectrum of surface active agents, however, there is great diversity of chemical structure and function. The concept of hydrophile-lipophile balance was developed in an effort to predict the function of surface active agents for making various types of emulsions and for other activities. Hydrophilic-lipophilic balance is a semi-empiric measurement of the relative strengths of the hydrophilic and hydrophobic components.[7] It is related to the free energy associated with positioning the amphyphilic molecule at the oil-water interface. The hydrophile-lipophile balance values required for various applications are shown in the following table:

TABLE I

Hydrophilic-Lipophilic Balance Ranges and Applications[8]

| Range | Application |
| --- | --- |
| 3 to 6 | water-in oil emulsifier |
| 7 to 9 | wetting agent |
| 8 to 13 | oil-in-water emulsifier |
| 13 to 15 | detergent |
| 15 to 18 | solubilizer |

These values are widely quoted in the literature as guides to the selection of emulsifiers for particular purposes. They are designed for use with nonionic emulsifiers. Analogous systems have been developed for anionic or cationic emulsifiers, but they are less useful than those for nonionic emulsifiers. Hydrophilic-lipophilic balance numbers have been published for many nonionic surfactants.[9]

In addition, Davies devised a method for calculating hydrophile-lipophile balance numbers for surfactants directly from their formula using empirically derived numbers.[10] Thus, a group number is assigned to various component groups in emulsifiers and the hydrophile-lipophile balance (HLB) is then calculated from the following relation:[11]

HLB=7+$\Sigma$ (hydrophilic group numbers)–$\Sigma$ (lipophilic group numbers):

HLB numbers have proved valuable guides for selecting emulsifiers in that emulsifiers outside of the specified range will seldom be efficacious for a particular application. However, a correct HLB number does not guarantee performance indicating that factors other than HLB are also important and must be considered. It should be noted that no applications are listed for surfactants with HLBs of less than three. Such agents have been used to spread bath oil on the surface of water, as vaccine adjuvants and for a few other applications. However, they are seldom used as emulsifying agents.

Most water-in-oil emulsions use surfactants with an HLB in the range of 3 to 6 as described above.[12] Finely divided solids may also be used as emulsifying agents. It has been reported that the objective in a water-in-oil emulsion is to produce an interfacial film with rigidity and no charge.[13] The stability of an emulsion can frequently be increased by increasing the concentration of emulsifying agent, but this increases problems of toxicity for biologic applications and may be suboptimal for other applications as well.

Emulsion stability is frequently increased when two surfactants with moderate differences in HLB and other properties are mixed together. If the differences are too large, however, then the combination seldom works. Attempts have been made to predict the function of blends of surfactants by averaging their HLB values, but instances are well known where blends produce results which are far different from the average of the components.[14] Mixed surfactants may produce a synergistic effect in stabilizing emulsions. This is thought to be related to the formation of structured complexes similar to liquid crystals at the oil-water interface. Phospholipids have been mixed with Span 80 to stabilize water-in-vegetable oil emulsions.[5]

Finally, heterogeneity of polyoxyethylene chain length frequently effects emulsion stability, especially in situations where the surfactant is marginally soluble. Preparations with increased heterogeneity of chain length tend to produce emulsions with greater stability. As can be seen from the foregoing discussion, it is difficult to predict the emulsifying properties of any combination of compounds based on the physical properties of the compounds.

Various oils differ markedly in the ease with which they can be emulsified and in the stability of the resulting emulsions. In general, mineral oil is easier to emulsify than vegetable oils.[16] Each oil has a required HLB number for production of a particular type of emulsion. This is the reason for the range of HLB numbers for production of each type of emulsion as shown in Table I. The more polar the oil phase, the more polar the surfactant must be to produce an optimum emulsion. Water-in-oil emulsions follow similar rules as oil-in-water emulsions, but the HLB values are lower. HLB values required to produce water-in-oil and oil-in-water emulsions with many commonly used oils have been published.[17]

Numerous methods have been devised for producing water-in-oil emulsions. Most of these involved mixing the components in a machine which produces agitation or a strong shear force. It has been recommended that oil-soluble materials be placed in the oil phase and water-soluble materials in the water phase prior to combining the phases.[18] However, this results in a less than satisfactory emulsion preparation. An exception to this is that very fine oil-in-water emulsions can be produced by placing a water soluble surfactant in the oil phase.[19] The reverse has not been recommended for water-in-oil emulsions. Placing hydrophobic surfactants in tie aqueous phase of an emulsion generally leads to poor emulsification. Fine oil-in-water emulsions can be prepared from water-in-oil emulsions by phase inversion. Many surfactants change their properties and switch from promoting one type of emulsion to the other with change in temperature.[20] This phenomena can be used to produce emulsions under certain circumstances.

Stabilizers for Water-in-Oil Emulsions

Prior art water-in-oil emulsions are difficult to stabilize. This has seriously impeded their application in many situations where they would otherwise be highly desirable. Stabilization has been attempted by increasing the viscosity of one or more of the phases or interfaces. That can be accomplished by adding polymeric stabilizers which form gels in the bulk phases or other structures at interfaces. Such polymers include proteins, starches, gums, cellulosics, polyvinyl alcohols, polyacrylic acid and polyvinyl pyrrolidone.[21] These materials bind to the interface by covalent bonds or by electrostatic and hydrophobic interactions. They form an "interfacial complex" which is defined as an association of two or more surface active molecules at an interface in a relationship that does not exist in either of the bulk phases. Certain complexes localized at the interface of oil-in-water in emulsions can be effective in stabilizing the emulsions. Some low molecular weight materials have similarly been used as stabilizers. These include cholesterol, which may form complexes with certain nonionic emulsifying agents.[22] In addition, fatty acid salts of divalent cations such as aluminum stearate are very effective in stabilizing water-in-oil emulsions. Salts of the same fatty acids with monovalent cations such as sodium stearate are not effective.

Problems with Prior Art Water-in-Oil Emulsions

The major problems impeding the increased use of water-in-oil emulsions are difficulty in preparation, high viscosity, and poor stability. Vegetable oils, such as peanut oil and soybean oil, or animal oil, such as squalene or squalane, would be preferable to mineral oil for many applications. However, they are more difficult to emulsify and make less stable emulsions. Water-in-oil emulsions of vegetable oil require relatively high concentrations of a hydrophobic emulsifier such as Span 80 and a stabilizer. Aluminum or magnesium stearate have been used successfully as stabilizers. However, they add to the complexity and toxicity of emulsions. Another problem is that the solubility of nonionic surfactants and thus their ability to produce stable emulsions varies with temperature. This produces problems in storage of emulsions where the temperature may vary from below freezing to greater than 120° F.

Many attempts to overcome these problems have involved polymerization of some component of the emulsion to produce increased rigidity. Polymers have been added to either the aqueous or oil phases which are then polymerized chemically or by radiation. Some surfactants can be polymerized at the oil-water interface with x-radiation. This is not useful for water-in-oil emulsions which require hydrophobic surfactants because these surfactants tend to be degraded by x-radiation.[23] Finally, heating to temperatures which denature proteins is required to melt or dissolve certain components of emulsions.[24] This precludes the use of such emulsions for many biologic activities where native, non-damaged proteins are required. Finally, very high concentrations of emulsifying agents may be needed. In one example, up to 82% of the oil phase of the emulsions was made up of the surfactant Pluronic® L121 (poloxamer 401).[25] Other examples in the same patent required heating to high temperatures to produce water-in-oil emulsions with block copolymer surfactants.

What is needed is an improved method of producing water-in-oil emulsions which does not require high temperatures, organic solvents, x-radiation or chemical reactions to cause crosslinking to form the desired emulsion. The method should optimally produce water-in-oil emulsions by spontaneous emulsification. In addition, the emulsions need increased stability. They should be stable at a high range of temperatures. Preferably, the emulsions should have lower toxicity to be useful for biologic applications. To do this, they should contain fewer components and the components that are present should be less toxic. Stabilizers should be reduced. The concentration of water in the water-in-oil emulsion should be increased to a higher level, preferably over 80%. Most water-in-oil emulsions have used less than 50% water. Finally, the water-in-oil emulsion should provide a good starting material for production of water-in-oil-in-water multiple emulsions.

Multiple Emulsions

The water-in-oil-in-water multiple emulsion comprises three distinct phases.[26] The innermost phase is aqueous. It is encapsulated in an oil phase which is, in turn, enclosed within a second aqueous phase. Each dispersed oil globule in a water-in-oil-in-water emulsion forms a vesicular structure with single or multiple aqueous compartments separated from the aqueous suspending fluid by a layer of oil phase components. Such emulsions have most of the advantages of water-in-oil emulsions with much lower viscosity. They also have many similarities with liposomes but have large aqueous compartments and can be prepared without inorganic solvents. Multiple emulsions can be considered a relatively unstable metaphase between water-in-oil and oil-in-water emulsions. The oil layer which separates the two aqueous phases may become very thin which is independent of the amount of the oil phase component(s). The stability of these emulsions may be phenomenologically understood as being brought about by the durability of the oil layer.[27] Rigid oil layers or films are associated by increased stability.

Multiple emulsions can be useful in many technologies, particularly in the pharmaceutical and in separation science. Their potential biopharmaceutical applications are unique as a consequence of the dispersal of one aqueous phase inside droplets of another. These include potential as vaccine adjuvants, drug delivery systems, sorbent reservoirs in drug overdose treatments and for immobilization of enzymes. They can also be used for separation of hydrocarbons and in the removal of toxic materials from waste water. Multiple emulsions according to the present invention can be formulated as cosmetics and as household products such as wax polish. They have been used to immobilize insulin for depot injection and in foods. The main problem associated with multiple emulsions is their instability which has severely limited their usefulness in the many applications for which they have shown obvious promise.[28]

Production of Multiple Emulsions

Multiple emulsions have been produced by several techniques which have advantages in different situations. However, none of them are optimal. One procedure involves the preparation of a water-in-oil emulsion which is then converted to a multiple emulsion by increasing the amount of water phase until the emulsifying capacity of the oil phase is exceeded. Alternatively, by changing the temperature past the inversion point, some emulsions will transform from water-in-oil to an oil-in-water producing a transient multiple emulsion phase.

Multiple emulsions having two different aqueous phases must be prepared in two steps. This is accomplished by producing a water-in-oil emulsion by any standard technique. This water-in-oil emulsion is then re-emulsified in the second aqueous phase which normally contains surfactants. Nonionic emulsifiers are usually preferable to ionic ones for the second step. Span 80 has been a successful emulsifier for the water-in-oil emulsion in the first step. "A large amount of Span 80 in liquid paraffin, however, is one of the necessary conditions for developing multiple emulsion type dispersions."[29] Less than 20% Span 80 results in an oil-in-water emulsion (see Table II). The optimal for paraffin oil is approximately 30%. For emulsification of animal oil or vegetable oils, even larger amounts of Span 80, in the order of 50%, are required. The water-in-oil emulsifier is always added to the oil phase of the emulsion. The concentration of hydrophilic emulsifier in the outer aqueous phase is also critical in that the concentration must be very small in relation to the concentration of hydrophobic emulsifier in the oil phase. For example, concentration of Tween 80 in the aqueous phase cannot exceed 1%, while Span 80 in the oil phase must be in excess of 30% to produce stable emulsion.[30]

TABLE II

| % Span 80 | Type of Emulsion | Multiple Emulsion Index |
| --- | --- | --- |
| 10 | o/w | 0 |
| 20 | o/w | 0 |
| 30 | w/o/w | 0.7 |
| 40 | w/o/w | .15 |
| 50 | w/o/w | .25 |
| 60 | w/o/w | .30 |
| 70 | w/o/w | .27 |
| 80 | w/o/w | .16 |
| 90 | w/o/w | .05 |
| 100 | w/o/w | 0 |

Table II: Effect of Span 80 concentration in the oil phase on the formation of water-liquid paraffin-water emulsions prepared by the mechanical agitation; concentration of SDS in the aqueous phase was fixed at 0.15M in all instances. The multiple emulsion index is a measure of the formation of w/o/w.[31]

A variety of stabilizing agents and regimens have been used in the prior art to increase the stability of multiple emulsions. Soy lecithin at a concentration of 8% allowed a reduction in the amount of Span 80 to 20% while maintaining stability of the emulsion. Like water-in-oil emulsions, the volume fraction of the oil phase is not critical. This is thought to be due to the fact that emulsion components are mobile and stability depends upon maintaining integrity of a lipid film as it thins.[32]

Like water-in-oil emulsions, vegetable oils and animal oils are more difficult to use in production of multiple emulsions than mineral oil. For example, 60% Span 80 is required to produce a multiple emulsion with olive oil.[33] This can be reduced to 43% if 17% soy lecithin is added. In addition, pairs of surfactants can be used to stabilize multiple emulsions in much the same manner that they have been used for w/o emulsions.

Block Copolymer Surfactants in Prior Art Multiple Emulsions

Copolymer Pluronic® L101 (poloxamer 331) has been used as the hydrophobic emulsifier in combination with Pluronic® P123 (poloxamer 403) as the hydrophilic emulsifier to produce water-in-oil-in-water multiple emulsions.[34, 35] The Pluronic® L101 at 5% in mineral oil was emulsified with saline containing 2% bovine serum albumin. Over time, the bovine serum albumin formed a complex with the Pluronic® L101 at the oil-water interface. This complex was thought to be important in maintaining the stability of the water-in-oil component of the emulsion. If the multiple emulsion is produced before this interfacial complex has time to form, the resulting water-in-oil-in-water emulsion is less stable. This emulsion was then re-emulsified in saline containing 0.4% Pluronic® P123. Several copolymer surfactants were evaluated in this study. Pluronic® L101 and P123 were found to be the most effective. Copolymers with hydrophobes larger than 4000 have not been evaluated.

Physical Stabilizers

Because of the inherent instability of multiple emulsions, several approaches to enhancing stability by producing physical rigidity have been tried.[36,37] One approach utilizes interaction between hydrophilic polymers in the inner aqueous phase with the surfactant. The BSA-L101 interaction described above is an example. Other examples used polyacrylic acid or polyelectrolytes with high molecular weights approaching three million. In addition, the surfactant on the interface has been crosslinked by x-radiation or polymerization of chemically reactive monomers.[38] This has been done to polymerize material in the inner aqueous phase, at the oil-water interface, in the oil phase, and in the outer aqueous phase. The oil droplets have been encapsulated with gelatin and other materials to provide physical barriers. While each of these methods has provided a measure of increased stability under certain conditions, the emulsions have seldom been sufficiently stable, nontoxic and functional to facilitate widespread use.

Problems with Multiple Water-in-Oil-in-Water Emulsions

As mentioned above, the primary problem in water-in-oil-in-water emulsions is stability. The inherent instability of multiple emulsions has precluded most commercial uses. However, there have been a few reports of attempts to improve stability. Procedures for increasing the stability of multiple emulsions have been rather empirical in that each manipulation tends to be highly specific for the particular emulsion under evaluation.[39] Nevertheless, some principals can be formulated. The most important problem appears to be the instability caused by the aqueous emulsifier in the outer layer which progressively solubilizes the hydrophobic emulsifier in the oil layer and destroys the internal emulsion.[40] The almost inevitable interaction of the surfactant used in the second emulsification step with the initial interfacial film demonstrates the inherent impracticality of employing free surfactant stabilizers in multiple emulsions. A more permanent interfacial membrane which does not permit diffusion of stabilizing components is preferable.

Assessment of Multiple Emulsions

Multiple emulsions have been classified as types A, B and C, depending upon the size and number of water droplets inside of the oil drops. Type A has a single water droplet, B a small number, and C a larger number of water drops within the oil drops.[41] According to this classification, the emulsions produced as Freund's complete adjuvant or the multiple emulsions of the present invention are much finer than even the C emulsions. It has been reported that multiple emulsions may be more stable than the original water-in-oil emulsions under certain conditions. In one example, soybean oil emulsified with glyceryl monooleate was stable at 80° C.[42] It is reported that multiple emulsions made with Freund's adjuvant are more stable than the parent water-in-oil emulsion in storage at 4° C.[43]

The overriding problem limiting the usefulness of multiple emulsions is stability. Most publications reporting on stability demonstrate unacceptable levels even for the more stable preparations. For biologic products, the emulsions should have a shelf life comparable to that of the contained drug in the refrigerator or freezer. In addition, many of the components used to increase stability will also increase toxicity. Multiple emulsions have usually used high concentrations of hydrophobic surfactants and stabilizers which are inherently toxic. In addition, a low concentration of water, less than 50% in the internal aqueous phase, forces an increase in the amount of oil for the amount of inner aqueous phase to be delivered. This is important because the inner aqueous phase is the site of choice for most active ingredients. Finally, it would be highly desirable to use a vegetable oil such as peanut oil or an animal oil (squalene or squalane) in place of the non-metabolizable mineral oil. However, multiple emulsions with vegetable oil have been even more difficult to produce and maintain stable than those with mineral oil.

SUMMARY OF THE INVENTION

The present invention comprises water-in-oil and water-in-oil-in-water multiple emulsions and the method of preparation which overcome many of the limitations of previous emulsions and are superior preparations for use in numerous applications including, but not limited to, vaccine adjuvants, oral, topical and parenteral drug delivery, pharmaceuticals, cosmetics, foods and various household and industrial uses.

The present invention is a stable water-in-oil emulsion containing a dispersed aqueous phase within a continuous oil phase, the aqueous phase having an effective amount of a first surfactant with a hydrophile-lipophile balance of less than approximately 2 and the continuous oil phase having a second surfactant.

The present invention also includes a stable water-in-oil-in-water multiple emulsion containing a dispersed inner aqueous phase within an oil phase which is in a continuous outer aqueous phase, the inner aqueous phase having an effective amount of a first surfactant with a hydrophile-lipophile balance of less than approximately 2 and the oil phase having a second surfactant. Optionally, a surfactant can be added to the continuous outer aqueous phase.

The preferred compound to be added to the inner aqueous phase is an effective amount of a surface active copolymer with the following general formula:

$$HO(C_2H_4O)_b(C_3H_6O)_a(C_2H_4O)_bH$$

wherein a is an integer such that the hydrophobe represented by $(C_3H_6O)$ has a mean molecular weight of approximately 3000 to 15000, with the preferable range between 3000 and 9000, and most preferably between approximately 5000 to 6000, and b is an integer such that the hydrophile portion represented by $(C_2H_4O)$ constitutes from about 2% to 19% by weight of the compound.

The copolymer Pluronic® 180.5 is the preferred surfactant. The formula for Pluronic® 180.5 is as follows:

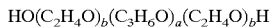

$$HO(C_2H_4O)_b(C_3H_6O)_a(C_2H_4O)_bH$$

wherein the mean molecular weight of the hydrophobe $(C_3H_6O)$ is approximately 5200 and the percentage of hydrophile $(C_2H_4O)$ is approximately 5% by weight.

Another preferred surfactant is Pluronic® L141 which has the following formula:

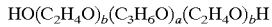

$$HO(C_2H_4O)_b(C_3H_6O)_a(C_2H_4O)_bH$$

wherein the mean molecular weight of the hydrophobe $(C_3H_6O)$ is approximately 4600 and the percentage of hydrophile $(C_2H_4O)$ is approximately 10% by weight.

The emulsions are typically made by mixing the components of the inner aqueous, oil and outer aqueous phases. If a block copolymer surfactant is to be included in the inner aqueous phase, it should be solubilized by refrigeration and allowed to precipitate by warming prior to emulsification. A water-in-oil (w/o) emulsion is prepared by any convenient method. This is then re-emulsified in the outer aqueous phase to prepare a multiple (w/o/w) emulsion. The w/o emulsion can be tested by placing a sample in water. The w/o/w emulsion is evaluated by several procedures. The simplest is microscopy.

Accordingly, it is an object of the present invention to provide compositions and methods for preparing water-in-oil and water-in-oil-in-water emulsions that are stable and useful in a wide variety of applications.

It is another object of the present invention to provide compositions and methods for preparing superior vaccine adjuvants.

It is another object of the present invention to provide compositions and methods for preparing emulsions that can be used as parenteral, topical, mucosal or oral drug delivery vehicles.

It is another object of the present invention to provide compositions and methods that can be used to prepare emulsions useful in formulating cosmetic preparations.

It is yet another object of the present invention to provide compositions and methods that can be used to prepare emulsions that are useful in the preparation of foods.

It is another object of the present invention to provide compositions and methods that can be used to prepare emulsions that are useful in separation science.

These and other objects, features and advantages of the present invention will become apparent after a review of the following detailed description of the disclosed embodiments and the appended claims.

BRIEF DESCRIPTION OF THE FIGURES

FIG. 1 is a grid showing the relationship between the various poloxamer compounds.

FIG. 2 shows the titers of secretory IgA in intestinal fluid following oral immunization with TNP-HEA in a water-in-oil-in-water emulsion.

FIG. 3 shows the serum titers of IgG and IgA following oral immunization with TNP-HEA in a water-in-oil-in-water emulsion.

FIGS. 4A and 4B illustrate comparative emulsion stability data generated by producing water-in-oil emulsions and water-in-oil-in-water emulsion wherein the emulsion stability of various emulsions comprising 3 mg/ml bovine serum albumin in the inner aqueous phase, a squalene oil phase, and a variety of surfactants and stabilizers, are compared.

FIGS. 5A and 5B illustrate comparative emulsion stability data generated by producing water-in-oil emulsions and water-in-oil-in-water emulsions wherein the emulsion stability of various emulsions comprising 3 mg/ml bovine serum albumin in the inner aqueous phase, no stabilizers in the inner aqueous phase, a squalene oil phase, and a variety of surfactants and stabilizers in the oil phase and the outer aqueous phase, are compared.

FIGS. 6A and 6B illustrate comparative emulsion stability data generated by producing water-in-oil emulsions and water-in-oil-in-water emulsions wherein the emulsion stability of various emulsions comprising 10 mg/ml bovine serum albumin in the inner aqueous phase, a squalene oil phase, and a variety of surfactants and stabilizers, are compared.

FIGS. 7A and 7B illustrate comparative emulsion stability data generated by producing water-in-oil emulsions and water-in-oil-in-water emulsions wherein the emulsion stability of various emulsions comprising 3 mg/ml bovine serum albumin in the inner aqueous phase, either poloxomer 520.5 (L180.5) or no stabilizers in the inner aqueous phase, a squalene oil phase, and a variety of surfactants and stabilizers in the oil phase and the outer aqueous phase, are compared.

FIGS. 8A, and 8B, and 8C illustrate comparative emulsion data generated by producing water-in-oil emulsions and water-in-oil-in-water emulsions wherein the emulsion stability of various emulsions comprising 3 mg/ml bovine serum albumin in the inner aqueous phase, either poloxomer 520.5 (L180.5) or no stabilizers in the inner aqueous phase, a variety of oil phases, and a variety of surfactants and stabilizers in the oil phase and the outer aqueous phase, are compared.

FIGS. 9A-1 through 9A-3 illustrate comparative emulsion stability data generated by producing water-in-oil emulsions and water-in-oil-in-water emulsions wherein the emulsion stability of various emulsions comprising 10 mg/ml bovine serum albumin in the inner aqueous phase, a peanut oil phase, and a variety of surfactants and stabilizers, are compared.

FIGS. 9B-1 through 9B-3 illustrate comparative emulsion stability data generated by producing water-in-oil emulsions and water-in-oil-in-water emulsions wherein the emulsion stability of various emulsions comprising chick embryo fibroblast culture cells and fluid in the inner aqueous phase, a peanut oil phase, and a variety of surfactants and stabilizers, are compared.

FIGS. 10A through 10D illustrate comparative emulsion stability data generated by producing water-in-oil emulsions and water-in-oil-in-water emulsions wherein the emulsion stability of various emulsions comprising 10 mg/ml bovine serum albumin in the inner aqueous phase, a variety of oil phases, and a variety of surfactants and stabilizers, are compared.

FIG. 11 illustrates comparative emulsion stability data generated by producing water-in-oil emulsions and water-in-oil-in-water emulsions wherein the emulsion stability of various emulsions comprising 3 mg/ml bovine serum albumin or saline in the inner aqueous phase, poloxomer 520.5 (L180.5) in the inner aqueous phase, a squalene oil phase, and variety of surfactants and stabilizers, are compared.

DETAILED DESCRIPTION

The novel emulsions of the present invention involve placing an insoluble surface active agent with an hydrophile-lipophile balance of less than approximately 2 in the inner aqueous phase. This is contrary to prior art which teaches that hydrophobic emulsifiers should be placed in the oil phase. Very hydrophobic emulsifiers placed in the aqueous phase in a finely dispersed form provide exceptional emulsion stability probably by forming a stable interfacial barrier at the oil/water interface.

The preferred compound to be added to the inner aqueous phase is an effective amount of a surface active copolymer with the following general formula:

wherein a is an integer such that the hydrophobe represented by $(C_3H_6O)$ has a mean molecular weight of approximately 3000 to 15,000, preferably from 5000 to 10,000, and b is an integer such that the hydrophile portion represented by $(C_2H_4O)$ constitutes from about 2% to 19% by weight of the compound.

The copolymer L310 was prepared by gel permeation fractionation of the Pluronic L180.5. The formula for L310 is calculated as follows:

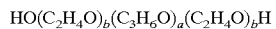

wherein the mean molecular weight of the hydrophobe $(C_3H_6O)$ is approximately 10,000 and the percentage of hydrophile $(C_2H_4O)$ is approximately 4% by weight.

The copolymer Pluronic® L180.5 is the preferred surfactant. The formula for Pluronic® L180.5 is as follows:

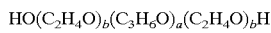

wherein the mean molecular weight of the hydrophobe ($C_3H_6O$) is approximately 5200 and the percentage of hydrophile ($C_2H_4O$) is approximately 5% by weight.

Another preferred surfactant is Pluronic® L141 which has the following formula:

wherein the mean molecular weight of the hydrophobe ($C_3H_6O$) is approximately 4600 and the percentage of hydrophile ($C_2H_4O$) is approximately 10% by weight.

The Pluronic® or poloxamer copolymer blocks are formed by condensation of ethylene oxide and propylene oxide at elevated temperature and pressure in the presence of a basic catalyst. There is some statistical variation in the number of monomer units which combine to form a polymer chain in each copolymer. The mean molecular weights given are approximations of the average weight of the copolymer molecules in each preparation. It is to be understood that the blocks of propylene oxide and ethylene oxide do not have to be pure. Small amounts of other materials can be admixed so long as the overall physical chemical properties are not substantially changed. A more detailed discussion of the preparation of these products is found in U.S. Pat. No. 2,674,619, which is incorporated herein by reference.

The nomenclature of the poloxamer compounds is based on a poloxamer grid (FIG. 1). The poloxamer grid is the relationship between nomenclature and composition of the various polymer members. The hydrophobe (polyoxypropylene) mean molecular weights are given as approximate midpoints of ranges. The first two digits of a poloxamer number on the grid, multiplied by 100, gives the approximate mean molecular weight of the hydrophobe. The last digit, times 10, gives the approximate weight percent of the hydrophile (polyoxyethylene) content of the surfactant.[44] For example, poloxamer 407, shown in the upper right hand quadrant of the grid (FIG. 1), is derived from a 4000 mean molecular weight hydrophobe with the hydrophile comprising 70% of the total mean molecular weight of the copolymer. Another example is poloxmer 760.5 which has a hydrophobe with a mean molecular weight of 7600 daltons and has a hydrophile which comprises 5% of the total mean molecular weight of the copolymer.

The emulsions of the present invention have a high degree of stability and can be prepared with up to approximately 90% to 95% water in the internal aqueous phase. The emulsion creams with partial coalescence of the oil droplets without breaking of the internal water-in-oil emulsion. Solubilization of the hydrophobic emulsifier by the hydrophilic emulsifier is largely eliminated. A common problem with multiple emulsions is that the hydrophilic surfactant in the outer aqueous phase leeches the hydrophobic surfactant out of the oil phase and solubilizes it in the outer aqueous phase. This destroys the oil phase emulsification capacity. By placing a hydrophobic surfactant in the inner aqueous phase, it is kept separate from the outer aqueous phase. The emulsifying capacity of the oil phase is not compromised by contact with the outer aqueous surfactant. Even though the oil phase droplets of the emulsions of the present invention may coalesce and fuse, there is little or no mixing of the inner and outer aqueous phases. Consequently, the multiple emulsions can be reformed merely by shaking the preparation. Water-in-oil emulsions can be formed spontaneously with up to 90% water. The new emulsions can reform after complete breakdown by moderate agitation. This is in contrast to most common water-in-oil emulsions with large proportions of water which cannot be reformed after breaking, except by separating the components and starting over.

The emulsions of the present invention are readily prepared and stable with various vegetable or animal oils, particularly peanut oil and squalene in addition to mineral oil. They can be prepared with between 10% and 95% water in the internal aqueous phase, however, for most purposes, the optimal water concentration lies between 60% and 80% volume/volume. The internal aqueous phase characteristically has a very fine droplet size. The preparations are stable frozen, refrigerated, at room temperature, and at elevated temperatures to a much greater extent than prior art preparations. They have an exceptionally low level of toxicity.

Emulsions of the present invention can be formed with a variety of different types of oils, hydrophobic surface active agents in the oil phase, and hydrophilic surface active agents in the outer aqueous phase. Oils that can be used according to the present invention include, but are not limited to, animal oils such as squalene or squalane, vegetable oils such as peanut oil, mineral oils such as drakeol, and synthetic oils such as isopropyl myristate. The oils and combinations of surfactants are well known to those skilled in the art. The emulsions can also utilize other stabilizing agents such as silica, aluminium stearate, bovine serum albumin, other proteins, and other polymerizing and stabilizing agents which are known to those skilled in the art. It is important to avoid the use of de-emulsifing agents.

The general preparation of the multiple emulsions of the present invention involves first mixing or homogenizing what will be the inner aqueous phase of the emulsion with a surfactant with a hydrophile-lipophile balance of less than approximately 2. Other materials may be mixed or dissolved in the inner aqueous phase. For example, if the emulsion is to be used as an adjuvant, the antigen can be placed in the aqueous phase. The preferred surfactants are the block copolymers discussed herein, but it is to be understood that other surfactants can be used as long such other surfactants have a hydrophile-lipophile balance of less than 2. The mixture is then homogenized with an oil to form a water-in-oil mixture.

Homogenization can be done by rapidly transferring the fluid between two syringes. Homogenization can also be done in a mini-blender, by sonication, or by any one of a number of methods that are well known to one of ordinary skill in the art. To produce a water-in-oil-in-water multiple emulsion, the water-in-oil emulsion is then homogenized with a second aqueous phase.

One application of the present invention is the preparation of effective vaccines against infections which can be used in any species of animal. Water-in-oil emulsions such as Freund's complete adjuvant and adjuvant 65 are known to be very effective in producing strong immune responses against a wide variety of antigens. Adjuvant 65 is a water-in-peanut oil emulsion which uses mannide monooleate as an emulsifier and aluminum stearate as a stabilizer. Adjuvant 65 has been evaluated in numerous animal and human studies.[45,46] Emulsions made according to the present invention are superior because they have lower toxicity, can be used with lower doses of oil and surface active agents, and produce equivalent or higher immune responses. They are particularly effective for producing single dose vaccines against tetanus and hepatitis B. The conversion of multiple dose vaccines to single dose vaccines is a priority goal of the World Health Organization. The formulations are also useful as vaccine adjuvants for diverse other conditions including malaria, AIDS, influenza and pneumococcal pneumonia.

As vaccines, the formulations have the advantages of allowing a reduced dose of antigen which is used in a more efficient manner. They are less denaturing to the antigen than mineral oil emulsions. This produces a higher proportion of effective antibody against native determinants of the infecting organism. The emulsions made according to the present invention utilize the adjuvant effect of block copolymers in addition to their emulsifying properties. (See U.S. patent application Ser. No. 07/544,831, now abandoned in favor of Continuation-in-Part Application Ser. No. 07/716,807, which is incorporated herein by reference.) When used with antigens, the emulsions encourage the production of antibody to a larger number of antigenic sights or epitopes on parasite antigens. These emulsions are relatively nontoxic because of the reduction in dose of oil, surfactant and stabilizing materials. They can be mixed with lipopolysaccharide, muramyldipeptide derivatives or other immunomodulating agents to modulate the isotype or balance between the antibody and the cell mediated immunity. Vaccines can thus be modulated to produce particular types of immune response which are particularly effective against specific diseases. Because the immunomodulating agents are contained within the inner phase of the emulsions, they can be used in lower doses with less systemic toxicity. When the emulsions produced according to the present invention are used as adjuvants, they can be injected by any convenient route intravenously, intramuscularly or subcutaneously, taken orally or applied by the mucosal or nasal route. The emulsions are stable indefinitely in the freezer which is a major advantage over alum adjuvanted vaccines which must be refrigerated. The requirement for refrigeration, the "cold train", is a major impediment to use of vaccines in much of the world.

Water-in-oil or multiple emulsions according to the present invention can be used as drug delivery vehicles for oral, topical or mucosal use. They have the unusual property of containing easily denatured materials such as proteins in saline or other non denaturing fluid during transit through the stomach and upper gastrointestinal tract. The material is delivered intact and with high efficiency to the lower gastrointestinal tract. Finding means to protect materials from digestion during passage through the upper gastrointestinal tract has long been an elusive goal of drug delivery research.

The multiple emulsions according to the present invention can be used for parenteral injection to produce sustained release of drugs or to target drugs to specific areas of the body, especially to areas with high concentrations of macrophages. Because multiple emulsions have many of the properties of liposomes, they can be used for any application where liposomes have been used or considered. They have the added advantage of a large aqueous inner compartment and can be produced without the use of organic solvents.[47] Such emulsions can be used for oral ingestion of drugs to promote sustained release and/or protect the drugs from digestion in the stomach due to acid and proteolytic enzymes. The emulsions according to the present invention can also facilitate absorption. In addition, the use of copolymers inhibit lipases and maintain emulsion integrity and drug delivery to the lower parts of the gastrointestinal tract. Multiple emulsions can also be used for delivery of drugs transmucosally through the nose, rectum, vagina or other mucus membranes. The tendency of multiple emulsions to spread on compatible surfaces facilitate drug delivery and absorption through any external or internal body surface.

A prior art water-in-oil emulsion, Freund's complete adjuvant, has been the most widely used immune adjuvant for immunizing animals. It is, however, too toxic for use in humans. A version without mycobacteria, Freund's incomplete adjuvant, was used in clinical vaccines but was abandoned for reasons of toxicity.[48,49,50,51] A peanut oil water-in-oil emulsion containing Arlacel A (mannide monooleate) and aluminium stearate was evaluated in the 1960's as an adjuvant for human vaccines.[52,53,54] It showed promise but was abandoned. One of the problems with these water-in-oil emulsion vaccines is that the dose of ¼ to ½ ml results in an excessively large injection of oil which has been associated with severe local and occasionally systemic toxic reactions.

Multiple emulsions with a high content of water and adequate stability have potential uses in foods, cosmetics, separation science, catalysis of chemical reactions and many other areas. Preparation of emulsions with very high content of water, and of multiple emulsions which lack irritating stabilizing agents, is a particular advantage in cosmetics.

Multiple emulsions have been proposed as use in multiple types of foods and sauces. The low toxicity of copolymers and the formation with edible oils provide excellent opportunities for food products.

Multiple emulsions prepared by the present invention can be used in nearly any application of separation science where other water-in-oil or water-in-oil-in-water emulsions have been prepared. The multiple emulsions provide a convenient vehicle for diffusion of materials across semipermeable membranes (the oil layer). In appropriate situations, this can be used to facilitate separation of materials. It has bee n proposed that such emulsions can be used for solvent extraction and as a method for treating drug overdosage.

MULTIPLE EMULSIONS ABBREVIATION AND RESULTS CODES

31R1 Meroxapol (Pluronic® R 31R1)
Al St aluminum stearate
Al St-1 10 mg/ml aluminum stearate
Al St-4 40 mg/ml aluminum stearate
Arlacel 186 nonionic surfactant mixture of mono and diglycerides
BSA-3 3 mg/ml bovine serume albumin in saline
BSA-10 10 mg/ml bovine serum albumin in saline
DDA dimethyldioctadecyl ammonium bromide
Drakeol 6VR light mineral oil
egg lec egg lecithin
F68 poloxamer 188 (Pluronic® F68)
iso myris isopropyl myristate
CEF chick embryo fibroblast culture cells and fluid
L101 poloxamer 331 (Pluronic® L101)
L121 poloxamer 401 (Pluronic® L121)
L141 poloxamer 461 (Pluronic® L141)
L180.5 poloxamer 520.5 (Pluronic® L180.5)
nd not done
Octadecyl octadecylamine
o/w oil-in-water emulsion
P123 poloxamer 403 (Pluronic® P123)
Palmi acid palmitic acid
plurocol 2010 polyoxypropylene (MW~2000)
plurocol 4010 polyoxypropylene (MW~3900)
RT room temperature
S80 Span 80, sorbitan monooleate
Sil-10 10 mg/ml 5 $\mu$m MIN-U-SIL (quartz particles)
Sil-50 50 mg/ml 5 $\mu$m MIN-U-SIL (quartz particles)
soy lec soy bean lecithin
Span 65 sorbitan tristearate T150R1 Tetronic® R T150R1
T1501 (Poloxamine) Tetronic® T1501
Tween 80 polyoxyethylene sorbitan monooleate
w/o water-in-oil emulsion
w/o/w water-in-oil-in-water emulsion The grading code found in the last two columns of FIGS. 4 through 11 is defined in the following table. The designation "0" is the least stable and breaks within seconds. The designation "4" is the most stable and will remain an emulsion for weeks or months under harsh conditions. The designation "c" implys that the water droplets in the oil coelesce but do not fuse or break.

| Stability | Time of Emulsion | Code |
|---|---|---|
| Immediate | Seconds | 0 |
| Fast | Hours | 1 |
| Slow | Days | 2 |
| Very Slow | Weeks | 3 |
| Stable | Weeks at harsh conditions | 4 |

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art, without departing from the spirit of the present invention and/or the scope of the appended claims.

EXAMPLE 1

Water-in-oil and multiple emulsions (water-in-oil-in-water) were prepared using the materials and proportions shown in FIGS. 4 through 11. The three phases (inner aqueous, oil and outer aqueous) were prepared first by mixing the components in the proportions shown. For example, in line 35 of FIG. 4, the inner aqueous phase was prepared by mixing copolymer L180.5 at 20% v/v with a solution of 3 mg/ml of BSA in physiologic saline. The mixture was placed in a refrigerator at 4° C. to allow the copolymer to enter solution. It was then warmed to precipitate the copolymer prior to use. The oil phase was prepared from a mixture of squalene with 20% volume Span 80. No stabilizer was used. If silica had been used as a stabilizer, it would have been mixed with the oil phase surfactant prior to combining with the oil. If aluminium stearate had been the stabilizer, the oil phase would be heated to 50° to 80° C. to dissolve it. The outer aqueous phase is a mixture of physiologic saline with 0.5% Tween 80 and 0.5% F68.

The water-in-oil emulsion is prepared first by homogenization using any suitable homogenizing device familiar to those skilled in the art. In this example, one part (1 ml) of the oil phase is homogenized with 1 ml of the inner aqueous phase to produce a water-in-oil emulsion. This emulsion can be tested by placing a drop on the surface of water. It should hold its shape and not disperse. The water-in-oil emulsion is then secondarily emulsified in 6 parts (6 ml) of the outer aqueous phase to produce a water-in-oil-in-water emulsion. This emulsion (line 35 of FIG. 4) was found to be highly stable following 24 hours at room temperature. Each of the other emulsions shown on FIGS. 4 through 11 were prepared by similar procedures.

A scheme for classifying multiple emulsions as types A, B and C was proposed by Florence. Type C is the best. The inner aqueous phase has many small water droplets. Type B is a less satisfactory emulsion in which the inner aqueous phase has several discrete water droplets. Type A, the poorest, has an inner aqueous phase with a single large droplet. The emulsion of this example was better than any described by Florence.[55] The inner aqueous droplets were so fine that individual droplets could not be seen with light microscopy. Rather, the emulsion appeared to have a ground glass appearance because of the myriad of very fine water droplets of the inner aqueous phase.

EXAMPLE 2

10% to 20% Span 80 in squalene is able to produce stable water-in-oil emulsions, but is unable to produce stable water-in-oil-in-water multiple emulsions (line 25–26; FIG. 4).

EXAMPLE 3

The addition of copolymers L121, L141 or L180.5 to 10% Span 80 in squalene reduces the ability to form a stable water-in-oil emulsion (lines 1–12; FIG. 4). Copolymers L121 and L180.5 destabilize the emulsions at concentrations of 8% in squalene while 20% of L141 is required.

EXAMPLE 4

Increasing the concentration of Span 80 to 20% of the oil phase overcomes the destabilizing ability of L141 and facilitates the preparation of a stable water-in-oil emulsion. Furthermore, the L141 in this situation promotes the formation of a stable multiple emulsion (lines 26 and 27; FIG. 4).

EXAMPLE 5

Either 1 or 4% aluminum stearate as a stabilizer in the oil phase overcomes the destabilizing ability of copolymer L141 and also promotes the formation of stable multiple emulsions (lines 28–31; FIG. 4).

EXAMPLE 6

Copolymers L141 or L180.5 added to the inner aqueous phase of an emulsion facilitate the formation of stable multiple emulsions. This is a surprising result since the literature teaches that hydrophobic surfactants should be placed in the oil phase. Furthermore, the HLB of these copolymers is lower than those reported for effective water-in-oil emulsifiers (lines 32–35 and 25–26; FIG. 4).

EXAMPLE 7

F68 is a more effective outer aqueous phase surfactant than Tween 80 for producing multiple emulsions (lines 1–9; FIG. 5).

EXAMPLE 8

If Span 80 and copolymer L180.5 are combined in the oil phase, increasing the concentration of Span 80 from 10% to 40% decreases the stability of the resulting multiple emulsion. This is to be contrasted with literature which states that multiple emulsions require high concentrations of Span 80 (lines 20–27; FIG. 5).

EXAMPLE 9

Copolymer L180.5 in the inner aqueous phase is superior to L141 or smaller copolymers for stabilizing multiple emulsions. This is clearly demonstrated when the concentration of water in the inner aqueous phase is raised to 80% of that of the water-in-oil emulsion (lines 1–6; FIG. 6).

EXAMPLE 10

Copolymer L180.5 effectively stabilizes multiple emulsions with 80% water in the internal aqueous phase.

These emulsions remain stable as viewed with light microscopy following storage at 37° C., 4° C., freezing at −20° C. and thawing over a period of several weeks (lines 1–6; FIG. 6).

EXAMPLE 11

Multiple emulsions with 80% water in the internal aqueous phase could be prepared with a large volume of outer aqueous phase without compromising stability. This is in contrast to the literature which teaches the importance of limiting the volume of the outer aqueous phase (lines 1–3 and 19–21; FIG. 6).

EXAMPLE 12

Copolymer L180.5 in the inner aqueous phase of water-in-oil emulsions with squalene increases the stability of the water-in-oil emulsion and very markedly increases the stability of multiple emulsions. The stability of multiple emulsions is dependent upon the type of surfactant in the outer aqueous phase. In preparations with copolymer L180.5 in the inner aqueous phase, a much wider variety of surfactants could be used in the outer aqueous phase (lines 7–12 and 19–24; FIG. 7).

EXAMPLE 13

A multiple emulsion with 10% copolymer L180.5 in the inner aqueous phase and 0.25% P123 as the outer aqueous phase surfactant consists of 80% water in the internal water-in-oil emulsion and 80% of the total volume being the outer aqueous phase so that the oil phase constituted only 4% of the total emulsion. This produced a highly stable multiple emulsion which withstood freezing and thawing 4 times over a 17 day interval, storage at refrigerator room temperature or 37° C. for extended periods without evidence of even minor deterioration (line 24; FIG. 7).

EXAMPLE 14

The ability of copolymer L180.5 to promote stability of water-in-oil and water-in-oil-in-water multiple emulsions was tested with several oils, hydrophobic oil phase surfactants, and stabilizers. Copolymer L180.5 in the internal aqueous phase increased the stability of both water-in-oil and multiple emulsions of peanut oil prepared with Span 80, Arlacel 186 or Span 80 plus aluminium stearate (lines 11–20; FIG.8). It had a similar effect with a mineral oil (Drakeol 6VR) (lines 21–30; FIG. 8). Copolymer L180.5 in the inner aqueous phase did not increase the stability of emulsions with isopropyl myristate or plurocols under these conditions of very high outer aqueous volume.

EXAMPLE 15

It has frequently been reported that it is difficult to make stable water-in-oil or water-in-oil-in-water multiple emulsions with vegetable oils. The ability of copolymer L180.5 in the inner aqueous phase to promote stability of such emulsions is demonstrated. Span 80 with peanut oil produces an oil-in-water emulsion even at only 50% water (line 16; FIG. 9A). If copolymer L180.5 is added to the inner aqueous phase, highly stable water-in-oil emulsions are produced with 50%, 70% or 90% water. The water-in-oil emulsions then form a stable multiple emulsion (lines 10–12; FIG. 9A). This emulsion was further tested by storage at freezing or 4° C. and was found to be stable under these conditions as well. Other stabilizing agents such as aluminum stearate were less effective by themselves but produced very stable emulsions when used in combination with copolymer L180.5 (lines 22–24, 28–30, and 31–36; FIG. 9A). Similar results were observed when the inner aqueous phase contained chick embryo fibroblasts and their culture media in a formulation used for vaccines (lines 37–72; FIG. 9B).

EXAMPLE 16

Several hydrophobic surface active agents were added to the internal aqueous phases of water-in-oil and multiple emulsions of squalene, peanut oil, mineral oil, and isopropyl myristate. The copolymer L180.5 markedly increased the stability of both the water-in-oil and multiple emulsions with each of these oils (lines 1–2, 13–14, 25–26 and 37–38; FIG. 10). Copolymer T1501 had a similar but lesser effect (lines 4, 16, 28 and 40; FIG. 10). DDA, soy lecithin, aluminium stearate, and octadecylamine all increase the stability of one or more of the water-in-oil emulsions when added to the inner aqueous phase (FIG. 10).

EXAMPLE 17

The effect of protein in the inner aqueous phase and the concentration of copolymer L180.5 were evaluated in the studies shown in FIG. 11. The maximal effect of copolymer L180.5 in stabilizing the multiple emulsions required a concentration of 5% or greater (lines 1–2, 11–12; FIG. 11). However, an effect was observed in the lowest concentration used 0.01% (lines 9, 19; FIG. 11). The presence of protein in the internal aqueous phase had no influence on the results. These preparations were all tested at room temperature and 4° C. with similar results. Further studies were done to evaluate the role of salt concentration on the stability of emulsions. Emulsions formed with distilled water in the internal aqueous phase were less stable than those formed with normal state saline. Similarly, salt concentration twice that of physiologic saline produced emulsions with lower stability. This is in keeping with previous results of others demonstrating that the type and amount of salt concentration is important in determining the stability of water-in-oil and multiple emulsions.

EXAMPLE 18

L101 added at 5% v/v to the oil phase of isopropyl myristate failed to form an 80% water-in-oil emulsion with saline containing BSA (line 6; FIG. 8). It also failed to form a multiple emulsion with saline containing P123 as the outer aqueous phase (line 6; FIG. 8). This is contrasted to the report of Law et al. who prepared both water-in-oil and w/o/w emulsions with these materials.[56] However, there are several essential differences between their work and the present invention. First, Law et al. described only a 50% oil water-in-oil emulsion. The present invention can be prepared in excess of 70% with a variety of oils including isopropyl myristate (line 3; FIG. 10). Second, their emulsification was carried out at 1200 plus/minus 200 RPM in a mechanical stirrer for 30 minutes to form a water-in-oil emulsion. The present invention emulsifications are typically done in five minutes or less using joined syringes in the fashion commonly used for preparing immunologic adjuvant emulsions.[57,58,59] This demonstrates the superiority of the present invention in that water-in-oil emulsions are much easier to prepare. Third, Law et al. teach that addition of surfactants such as Span 80 to the oil of their emulsions cause extensive coalescence. Span 80 is an effective oil phase emulsifier in many examples of the present invention with a variety of oils including isopropyl myristate (line 37–38; FIG. 10). Fourth, Law et al. teach that the formation of multiple emulsions using these materials requires that the water-in-oil emulsion be aged overnight before preparation of the w/o/w emulsion. This allows interaction of the protein and copolymer L101. Their paper "Stabilization of w/o/w multiple emulsions by interfacial complexation of macromolecules and nonionic surfactants" identifies this phenomenon as necessary for stability of their emulsions.[60] Law et al. clearly identify maintaining separation of the surfactants across the oil layer as an important factor in the stability of w/o/w emulsions, but the solution they teach is quite different from the present invention. The emulsions of the present invention are prepared under much gentler conditions, contain higher proportions of water, are more stable and require no waiting period following preparation of the water-in-oil emulsion.

EXAMPLE 19

Current vaccines for hepatitis B infection are safe and effective but require a minimum of three injections over a period of several months to achieve a protective antibody titer of 10 mIU/ml in the majority of people.[61] A multiple emulsion was prepared and tested as a vaccine for the surface antigen of hepatitis B virus. The internal aqueous phase consisted of copolymer L180.5 (10 mg) mixed with 130 $\mu$g of plasma derived hepatitis B surface antigen (HBsAg) in 0.1 ml saline and refrigerated to dissolve the copolymer. The oil phase consisted of 0.08 ml of a mixture of 90% squalene and 10% Span 80. A water-in-oil emulsion was prepared by placing the internal aqueous phase and oil phases in a 1 ml plastic conical tube and drawing the mixture repeatedly through a blunt 18 gauge needle into an 1 ml plastic syringe. A thick water-in-oil emulsion formed in less than 30 seconds. This was converted to a water-in-oil multiple emulsion by addition of 0.22 ml of saline containing 0.25% Pluronic P103 (poloxamer 404) as the outer aqueous phase. The mixture was drawn through the 18 gauge needle to disperse the water-in-oil emulsion into a multiple emulsion.

The resulting multiple emulsion consisted of droplets of water-in-oil emulsion with a mean size of around 10 microns and internal water drops to small to be discerned with a light microscope. It was stable at room temperature for over four months. Similar preparations were stable through five freeze-thaw cycles.

The emulsion was injected subcutaneously into the flanks of ICR outbred mice in a volume of 0.05 ml which contained 1.23 mg of copolymer L180.5, 1.03 mg Span 80, 16 $\mu$g antigen and 9.25 mg squalene. All mice produced titers greater than 10 mIU/ml by 14 days. At 28 days, the mean titer was 20,815 mIU/ml. The local inflammatory response was minimal.

EXAMPLE 20

Examples 20 through 22 demonstrate how a water-in-oil emulsion according to the present invention can be used to deliver an active ingredient as a topical therapeutic. A 40 year old white female is treated with a water-in oil-emulsion (75% water) using Pluronic L180.5 in the aqueous phase and squalene +10% Span 80 as the oil phase, with a final concentration of 5% dermatan sulfate (Scientific Protein Labs, Waunakee, Wis.) for a severe radiation bum to the head.

The patient received 15 doses of total brain radiation for a metastatic adenocarcinoma in the left temporal lobe of her brain. The patient lost all of her hair. She received conventional therapy consisting of topical treatment of aloe gel and lanolin for the bums on her head. The bums were especially severe on her forehead.

The patient suffered from severe pain and itching. The patient's scalp was covered with red inflamed welts. Behind the patient's ear where the tumor was targeted with high dose radiation, the skin was cracked, red, swollen and very dry. The water-in-oil emulsion is applied to her entire scalp and forehead. The patient immediately had relief from the itching. Twelve hours after the first treatment, all of the red inflamed welts on her head were completely gone. The skin on her forehead was soft and supple Using the water-in-oil emulsion, the patient was essentially itch free for 12 hours. The patient was able to sleep without medication for the first time in weeks.

EXAMPLE 21

50 ml of a 70% water-in-oil emulsion containing 5% dermatan sulfate is administered to a 61 year old white male who has suffered from severe "contact" dermatitis for over 5 years. The patient's most severe problem is with his hands and especially during cold weather. Between the patient's fingers, the skin cracks and bleeds and his entire hand has a scaly scalded look. The patient's hands itch to the point that during his sleep he has scratched them until they bled. The patient applied the w/o emulsion twice a day, in the morning and at night. Within a few hours after the first treatment the pain and itching were relieved. After the patient used the emulsion for one week, the skin was supple and had a normal skin appearance.

EXAMPLE 22

A 30 year old white male was treated for a severe sunburn covering the entire back. The patient had exposed his back to the sun for approximately 7 hours with minimum sunscreen. The next day, the pain was so severe that the patient was nauseated. The patient was treated 48 hours after receiving the sunburn with the same water-in-oil emulsion used in Example 20. Within approximately 30 minutes, the pain and itching were relieved. The preparation was applied twice daily. Twenty-four hours after the first application all redness and inflammation were gone. He used the preparation for three more days and the skin healed completely.

EXAMPLE 23

A water-in-oil-in-water multiple emulsion consisting of 50% v/v of an outer aqueous phase of saline with 0.25% copolymer P123 was prepared. The other 50% v/v was a dispersed water-in-oil phase consisting of 72% saline, 18% squalene, 2% Span 80 and 32 mg copolymer L310 and 0.5 mg TNP-HEA per 0.5 ml of emulsion. The emulsion was administered to OCR outbred mice orally in a dose of 0.5 ml/mouse. The multiple emulsion was examined under a 200× magnification microscope. The microscopic appearance of the emulsion was 1.0 to 20$\mu$ diameter particles of water-in-oil emulsion. Transilluminated opened distal ileum of a mouse, 6 hours after gastric administration of the emulsion, showed emulsion particles associated with dome of a Peyers Patch (P). Because protein antigen is suspended in saline in the emulsion, this experiment suggests that water-in-oil emulsions are able to deliver native antigen to gut-associated lymphoid tissue. The emulsion was grossly visible and consisted of intact water-in-oil particles microscopically. A sample of cecal contents was removed at six hours after oral administration, examined by Ouchterlony analysis and found to contain antigenically intact TNP-HEA. Secretory IgA levels were measured following oral immunization of an antigen in a water-in-oil emulsion. The water-in-oil emulsion (0.5 ml) with TNP-HEA in the inner aqueous phase was infused intragastrically into groups of 6 outbred ICR mice on days 0, 14 and 34. Other groups received identical emulsions containing 100 μg detoxified RaLPS, Saponin or Silica as adjuvants. Circulating IgG and IgA antibody titers were measured following oral immunization. The serum samples were collected simultaneously with the intestinal fluid from the mice. The results are shown in FIGS. 2 and 3. In most cases, administration of the TNP-HEA antigen with emulsion alone gave the highest titers in both the intestinal fluid and in serum. When the TNP-HEA is administered orally in saline, there is no immune response either in the gut or in the serum.

It should be understood, of course, that the foregoing relates only to preferred embodiments of the present invention and that numerous modifications or alterations may be made therein without departing from the spirit and the scope of the invention as set forth in the appended claims.

[1] Becher P. Macroemulsions. Nonionic Surfactants Physical Chemistry. Edited by Martin J. Schick. Marcel Decker, 1987. pp 435–492
[2] Becher, P. Medical and Pharmaceutical Applications of Emulsions. Chapter 3 of Encyclopedia of Emulsion Technology, volume 2. Marcel Dekker, N.Y. 1985. ISBN 0-8247-1877-1 (v.2) at page 160
[3] Myers D. Surfaces, Interfaces and Colloids. VCH Publishers, Inc. 1990. at page 232
[4] Myers, D. Supra at page 232
[5] Myers, D. Supra at page 222
[6] Schulman J. H. and Cockbain E. G. Molecular interactions at oil/water interfaces. Part I. Molecular complex formation and the stability of oil in water emulsions. *Trans. Faraday Soc.*, 36:651–661, 661–668, 1940.
[7] Marszall L. HLB of nonionic surfactants: PIT and EIP methods. Nonionic Surfactants Physical Chemistry. Edited by Martin J. Schick. Marcel Decker, 1987. pp 493–548.
[8] Becher P. Macroemulsions. Nonionic Surfactants Physical Chemistry. Edited by Martin J. Schick. Marcel Decker, 1987. pp 435–492, at page 440
[9] Becher P. Supra at pg 443
[10] Becher P. Supra at pg 441
[11] Becher P. Supra at pg 441
[12] Becher P. Supra at pg 440
[13] Schulman J. H. et al. Molecular interactions at oil/water interfaces. Part I. Molecular complex formation and the stability of oil in water emulsions. *Trans. Faraday Soc.*, 36:651–661, 661–668, 1940.
[14] Matsumoto S. W/O/W-type multiple emulsions. Nonionic Surfactants Physical Chemistry. Edited by Martin J. Schick. Marcel Decker, 1987. pp 549–600, at page 535
[15] Matsumoto S., Supra at page 569
[16] Becher P. Supra at pg 462
[17] Myers D. Surfaces, Interfaces and Colloids. VCH Publishers Inc. 1990
[18] Guthauser B. Stable water-in-oil emulsions. U.S. Pat. No. 4,384,974. May 24, 1983.
[19] Guthouser, U.S. Pat. No. 4,384,974
[20] Becher P. Supra at pg 476
[21] Myers D., Supra at
[22] Schulman J. H. et al. Supra
[23] Florence A. T. and Whitehill D. Multiple w/o/w emulsions stabilized with poloxamer and acrylamide gels. *J. Pharm. Pharmacol* 32:64P, 1980
[24] Guthouser, U.S. Pat. No. 4,384,974
[25] Guthouser, U.S. Pat. No. 4,384,974
[26] Matsumoto S., Supra
[27] Matsumoto S., Supra
[28] Florence A. T., et al. The formulation and stability of multiple emulsions. *International Journal of Pharmaceutics,* 11:277–308, 1982
[29] Matsumoto S., Supra, at page 555
[30] Matsumoto S., Supra
[31] Matsumoto S., Supra, at page 556
[32] Matsumoto S., Supra, at page 563
[33] Matsumoto S., Supra, at page 593
[34] Law T. K., et al. Release from multiple w/o/w emulsions stabilized by interfacial complexation. *J. Pharm. Pharmacol.* 36:50P, 1984
[35] Law T. K., et al. Stabilization of w/o/w multiple emulsions by interfacial complexation of macromolecules and nonionic surfactants. *J. of Controlled Release* 3:279–290, 1986
[36] Florence A. T., et al. Supra
[37] Law T. K., et al., *J. of Controlled Release,* Supra
[38] Law T. K., et al., *J. of Controlled Release,* Supra
[39] Myers D., Supra at page
[40] Matsumoto S., Supra
[41] Florence A. T. and Whitehill D. Some features of breakdown in water-in-oil-in-water multiple emulsions. *J. of Colloid and Interface Science,* 79:243–256,1981
[42] Matsumoto S., Supra, at page 573
[43] Herbert W. J. Multiple emulsion adjuvants. *International Symposium on Adjuvants of Immunity.* 6:89–92, 1967.
[44] Henry, R. L., et al., "Burn Wound Coverings and the Use of Poloxamer Preparations", CRITICAL REVIEWS IN BIOCOMPATIBILITY, Vol. 5, No. 3, pp. 207–220 (1989).
[45] Hilleman M. R., Woodhour A., Friedman A., Weibel R. E. and Stokes J. The clinical application of adjuvant 65. *Annals of Allergy,* 30:152–158, 1972
[46] Hilleman M. R. Considerations for safety and application of emulsified oil adjuvants to viral vaccines. *International Symposium on Adjuvants of Immunity.* 6:13–26, 1967
[47] Lin T., and Lin S. Encapsulation and prolonged release behavior of w/o/w type multiple emulsions. *J. of the Chinese Chemical Society,* 35:463–470, 1988
[48] Stone H. D., Brugh M. and Beard C. W. Influence of formulation on the efficacy of experimental oil-emulsion newcastle disease vaccines. Avian Diseases, 27:688–697, 1983
[49] Herbert W. J. Some investigations into the mode of action of the water-in-mineral-oil emulsion antigen adjuvants. International Symposium on Adjuvants of Immunity. 6:213–230, 1967
[50] Holt L. B. Oily adjuvants. International Symposium on Adjuvants of Immunity. 6:131–136, 1967
[51] Herbert W. J. Some observations of practical interest in the use of water-in-mineral-oil emulsion antigen adjuvant. International Symposium on Adjuvants of Immunity. 6:251–256, 1967
[52] Hilleman M. R., Woodhour A., Friedman A., Weibel R. E. and Stokes J. The clinical application of adjuvant 65. Annals of Allergy, 30:152–158, 1972
[53] Woodhour A. F., Metzgar D. P., Stim T. B., Tytell A. A. and Hilleman M. R. New metabolizable immunologic adjuvant for human use. I. Development and animal immune response. New Adjuvant Development, PSAM 116:516–523, 1964
[54] Hilleman M. R. Considerations for safety and application of emulsified oil adjuvants to viral vaccines. *International Symposium on Adjuvants of Immunity.* 6:13–26, 1967

[55] Florence A. T. and Whitehill D. Some features of breakdown in water-in-oil-in-water multiple emulsions. *J. of Colloid and Interface Science,* 79:243–256,1981

[56] Law T. K., Whateley T. L. and Florence A. T. Stabilization of w/o/w multiple emulsions by interfacial complexation of macromolecules and nonionic surfactants. J. of Controlled Release 3:279–290, 1986

[57] Herbert W. J. Some investigations into the mode of action of the water-in-mineral-oil emulsion antigen adjuvants. International Symposium on Adjuvants of Immunity. 6:213–230, 1967

[58] Holt L. B. Oily adjuvants. International Symposium on Adjuvants of Immunity. 6:131–136, 1967

[59] Herbert W. J. Some observations of practical interest in the use of water-in-mineral-oil emulsion antigen adjuvant. International Symposium on Adjuvants of Immunity. 6:251–256, 1967

[60] Law T. K., Whateley T. L. and Florence A. T. Stabilization of w/o/w multiple emulsions by interfacial complexation of macromolecules and nonionic surfactants. J. of Controlled Release 3:279–290, 1986

[61] Francis D. P., Hadler S. C., Thompson S. E. et al. Ann Intern Med 1982; 97:362–66

We claim:

1. A vaccination method comprising administering to a patient a water-in-oil emulsion vaccine comprising an immunologically effective amount of an antigen, a first surfactant comprising, a polyoxyethylene polyoxypropylene block copolymer having the following formula:

$$HO(C_2H_4O)_b(C_3H_6O)_a(C_2H_4O)_bH$$

wherein the mean molecular weight of the hydrophobe ($C_3H_6O$) is between 5,000 to 15,000 Daltons and the percentage of hydrophile $C_2H_4O$) is between approximately 2% and 15% by weight the block copolymer having a hydrophile-lipophile balance of less than 2, and a continuous oil phase, prepared by the process comprising the steps of:

A. first homogenizing the antigen and the block copolymer in an aqueous phase to form an inner aqueous phase; and B. homogenizing the inner aqueous phase with an amount of oil sufficient to form a continuous oil phase, to form a water-in-oil emulsion having the inner aqueous phase dispersed in the continuous oil phase.

2. The method of claim 1 wherein the water-in-oil emulsion further comprises a second surfactant in the continuous oil phase.

3. The method of claim 1 wherein the administration is by oral administration.

4. The method of claim 1, wherein the first surfactant has the following formula:

$$HO(C_2H_4O)_b(C_3H_6O)_a(C_2H_4O)_bH$$

wherein the mean molecular weight of the hydrophobe ($C_3H_6O$) is approximately 10,000 Daltons and the percentage of hydrophile ($C_2H_4O$) is approximately 4% by weight.

5. The method of claim 1, wherein the first surfactant has the following formula:

$$HO(C_2H_4O)_b(C_3H_6O)_a(C_2H_4O)_bH$$

wherein the mean molecular weight of the hydrophobe ($C_3H_6O$) is approximately 5,200 Daltons and the percentage of hydrophile ($C_2H_4O$) is approximately 5% by weight.

6. The method of claim 1, wherein the oil is selected from the group consisting of vegetable oil, animal oil, mineral oil, isopropyl myristate and polyoxypropylene.

7. The method of claim 2, wherein the second surfactant is selected from the group consisting of poloxamer 331, poloxamer 461, poloxamer 520.5, sorbitan monooleate, sorbitan tristearate, and Arlacel 186.

8. A vaccination method comprising administering to a patient a water-in-oil-in-water emulsion vaccine comprising an immunologically effective amount of an antigen, a first surfactant comprising a polyoxyethylene polyoxypropylene block copolymer having the following formula:

$$HO(C_2H_4O)_b(C_3H_6O)_a(C_2H_4O)_bH$$

wherein the mean molecular weight of the hydrophobe ($C_3H_6O$) is between 5,000 to 15,000 Daltons and the percentage of hydrophile $C_2H_4O$) is between approximately 2% and 15% by weight, the block copolymer having a hydrophile-lipophile balance of less than 2, and a continuous oil phase, prepared by the process comprising the steps of:

A. first homogenizing the antigen and the block copolymer in an aqueous phase to form an inner aqueous phase;

B. homogenizing the inner aqueous phase with an amount of oil sufficient to form a continuous oil phase, to form a water-in-oil emulsion having the inner aqueous phase dispersed in the continuous oil phase; and C. homogenizing the continuous oil phase in a second aqueous phase to form an outer aqueous phase, to form a water-in-oil-in-water emulsion having the continuous oil phase dispersed in the outer aqueous phase.

9. The method of claim 8, wherein the water-in-oil-in-water emulsion further comprises a second surfactant in the continuous oil phase.

10. The method of claim 8, wherein the administration is by oral administration.

11. The method of claim 9, wherein the second surfactant is selected from the group consisting of poloxamer 331, poloxamer 461, poloxamer 520.5, sorbitan monooleate, sorbitan tristearate, and Arlacel 186.

12. The method of claim 8, wherein the outer aqueous phase contains a third surfactant selected from the group consisting of poloxamer 403, polyoxyethylene sorbitan monooleate, poloxamer 188 and mixtures thereof.

* * * * *